US012564344B2

(12) United States Patent
Lange et al.

(10) Patent No.: US 12,564,344 B2
(45) Date of Patent: Mar. 3, 2026

(54) METHODS AND SYSTEMS FOR ENGINEERING CARDIAC WAVEFORM FEATURES FROM BIOPHYSICAL SIGNALS FOR USE IN CHARACTERIZING PHYSIOLOGICAL SYSTEMS

(71) Applicant: Analytics for Life Inc., Toronto (CA)

(72) Inventors: Emmanuel Lange, Toronto (CA);
Farhad Fathieh, North York (CA)

(73) Assignee: Analytics for Life Inc., Toronto (CA)

( * ) Notice: Subject to any disclaimer, the term of this patent is extended or adjusted under 35 U.S.C. 154(b) by 313 days.

(21) Appl. No.: 17/891,533

(22) Filed: Aug. 19, 2022

(65) Prior Publication Data

US 2023/0076069 A1     Mar. 9, 2023

Related U.S. Application Data

(60) Provisional application No. 63/236,193, filed on Aug. 23, 2021.

(51) Int. Cl.
A61B 5/24        (2021.01)
A61B 5/349       (2021.01)
A61B 5/00        (2006.01)

(52) U.S. Cl.
CPC ............... A61B 5/24 (2021.01); A61B 5/349 (2021.01); *A61B 5/7267* (2013.01)

(58) Field of Classification Search
CPC ..... A61B 5/0006; A61B 5/0022; A61B 5/349; A61B 5/7264; A61B 5/4836; A61B 5/02;
(Continued)

(56) References Cited

U.S. PATENT DOCUMENTS 8,923,958 B2    12/2014  Gupta et al.
9,289,150 B1     3/2016  Ramchandani et al.
(Continued)

FOREIGN PATENT DOCUMENTS

WO       2010084211 A1    7/2010
WO       2017033164 A1    3/2017
(Continued)

OTHER PUBLICATIONS

International Search Report and Written Opinion, mailed Dec. 12, 2022, received in connection with corresponding International Patent Application No. PCT/IB2022/057803.
(Continued)

*Primary Examiner* — Deborah L Malamud
(74) *Attorney, Agent, or Firm* — Meunier Carlin & Curfman LLC

(57)                ABSTRACT

A clinical evaluation system and method are disclosed that facilitate the use of one or more morphologic atrial depolarization waveform-based features or parameters determined from biophysical signals such as cardiac or biopotential signals that are acquired, in preferred embodiments, non-invasively from surface sensors placed on a patient while the patient is at rest. Morphologic atrial depolarization waveform-based features or parameters can be used in a model or classifier to estimate metrics associated with the physiological state of a patient, including the presence or non-presence of a disease, medical condition, or an indication of either. The estimated metric may be used to assist a physician or other healthcare provider in diagnosing the presence or non-presence and/or severity and/or localization of diseases or conditions or in the treatment of said diseases or conditions.

19 Claims, 14 Drawing Sheets

(58) Field of Classification Search
CPC .. A61B 5/346; A61B 5/28; A61B 5/00; A61B 5/24; A61B 5/308
See application file for complete search history.

(56) References Cited

U.S. PATENT DOCUMENTS

| | | | |
|---|---|---|---|
| 9,408,543 | B1 | 8/2016 | Exner et al. |
| 9,597,021 | B1 | 3/2017 | Howe-Patterson et al. |
| 9,655,536 | B2 | 5/2017 | Yazdi et al. |
| 9,737,229 | B1 | 8/2017 | Burton et al. |
| 9,910,964 | B2 | 3/2018 | Burton et al. |
| 9,955,883 | B2 | 5/2018 | Burton et al. |
| 9,968,265 | B2 | 5/2018 | Gupta et al. |
| 9,968,275 | B2 | 5/2018 | Burton et al. |
| 10,039,468 | B2 | 8/2018 | Exner et al. |
| 10,292,596 | B2 | 5/2019 | Crawford et al. |
| 10,362,950 | B2 | 7/2019 | Burton et al. |
| 10,542,897 | B2 | 1/2020 | Crawford et al. |
| 10,566,091 | B2 | 2/2020 | Ramchandani et al. |
| 10,566,092 | B2 | 2/2020 | Burton et al. |
| 10,672,518 | B2 | 6/2020 | Burton et al. |
| 10,806,349 | B2 | 10/2020 | Crawford et al. |
| 2016/0022164 | A1 | 1/2016 | Gupta et al. |
| 2016/0287166 | A1* | 10/2016 | Tran ......................... A61B 5/74 |
| 2018/0000374 | A1 | 1/2018 | Gupta et al. |
| 2018/0249960 | A1 | 9/2018 | Gupta et al. |
| 2019/0026430 | A1 | 1/2019 | Grouchy et al. |
| 2019/0026431 | A1 | 1/2019 | Grouchy et al. |
| 2019/0076044 | A1 | 3/2019 | Krubsack et al. |
| 2019/0200893 | A1 | 7/2019 | Grouchy et al. |
| 2019/0214137 | A1 | 7/2019 | Gupta et al. |
| 2019/0365265 | A1 | 12/2019 | Grouchy et al. |
| 2019/0384757 | A1 | 12/2019 | Garrett et al. |
| 2020/0029842 | A1 | 1/2020 | Felix et al. |
| 2020/0085311 | A1 | 3/2020 | Tzvieli et al. |
| 2020/0138291 | A1* | 5/2020 | Bardy .................... A61B 5/259 |
| 2020/0205739 | A1 | 7/2020 | Garrett et al. |
| 2020/0205745 | A1 | 7/2020 | Khosousi et al. |
| 2020/0211713 | A1 | 7/2020 | Shadforth et al. |
| 2020/0229724 | A1 | 7/2020 | Gupta et al. |
| 2020/0335217 | A1 | 10/2020 | Burton et al. |
| 2020/0397322 | A1 | 12/2020 | Paak et al. |
| 2020/0397324 | A1 | 12/2020 | Paak et al. |
| 2021/0212582 | A1 | 7/2021 | Fathieh et al. |
| 2022/0192596 | A1 | 6/2022 | Fathieh et al. |
| 2023/0055617 | A1 | 2/2023 | Lange et al. |
| 2023/0071085 | A1 | 3/2023 | Doomra |
| 2023/0071467 | A1 | 3/2023 | Burton et al. |
| 2023/0072281 | A1 | 3/2023 | Fathieh et al. |
| 2023/0075570 | A1 | 3/2023 | Fathieh |
| 2023/0075634 | A1 | 3/2023 | Fathieh et al. |
| 2023/0127355 | A1 | 4/2023 | Paak et al. |

FOREIGN PATENT DOCUMENTS

| | | |
|---|---|---|
| WO | 2017221221 A1 | 12/2017 |
| WO | 2018158749 A1 | 9/2018 |
| WO | 2019077414 A1 | 4/2019 |
| WO | 2019130272 A1 | 7/2019 |
| WO | 2019130273 A1 | 7/2019 |
| WO | 2019234587 A1 | 12/2019 |
| WO | 2019244043 A1 | 12/2019 |
| WO | 2020136569 A1 | 7/2020 |
| WO | 2020136570 A1 | 7/2020 |
| WO | 2020136571 A1 | 7/2020 |
| WO | 2020254881 A1 | 12/2020 |
| WO | 2020254882 A1 | 12/2020 |

OTHER PUBLICATIONS

International Preliminary Report on Patentability, issued Feb. 27, 2024, received in connection with corresponding International Patent Application No. PCT/IB2022/057803.

Farhad, F. et al., Predicting cardiac disease from interactions of simultaneously-acquired hemodynamic and cardiac signals, Computer Methods and Programs in Biomedicine, vol. 202, Apr. 2021.

Cho et al., "A preliminary study on photoplethysmogram (PPG) signal analysis for reduction of motion artifact in frequency domain," 2012 IEEE-EMBS Conference on Biomedical Engineering and Sciences, Langkawi, pp. 28-33 (2012). doi: 10.1109/IECBES.2012.6498141.

Extended European Search Report issued on Sep. 4, 2025 in corresponding EP Application No. 22860724.8, 11 pages.

Purnawirawan, Anton et al., "Classification of P-wave Morphology Using New Local Distance Transform and Random Forests", 6th International Conference on Science and Technology (ICST), IEEE, vol. 1, Sep. 7, 2020 (Sep. 7, 2020), 6 pages.

Rowlands, David Duanne et al., "Estimating left atrial enlargement parameters from the electrocardiogram using wavelets", Journal of Electrocardiology, Apr. 11, 2022, vol. 44, No. 6, 4 pages.

Mike Cadogan and Robert Buttner Mike et al., "P wave—LITFL—ECG Library Basics", Jan. 29, 2022.

* cited by examiner

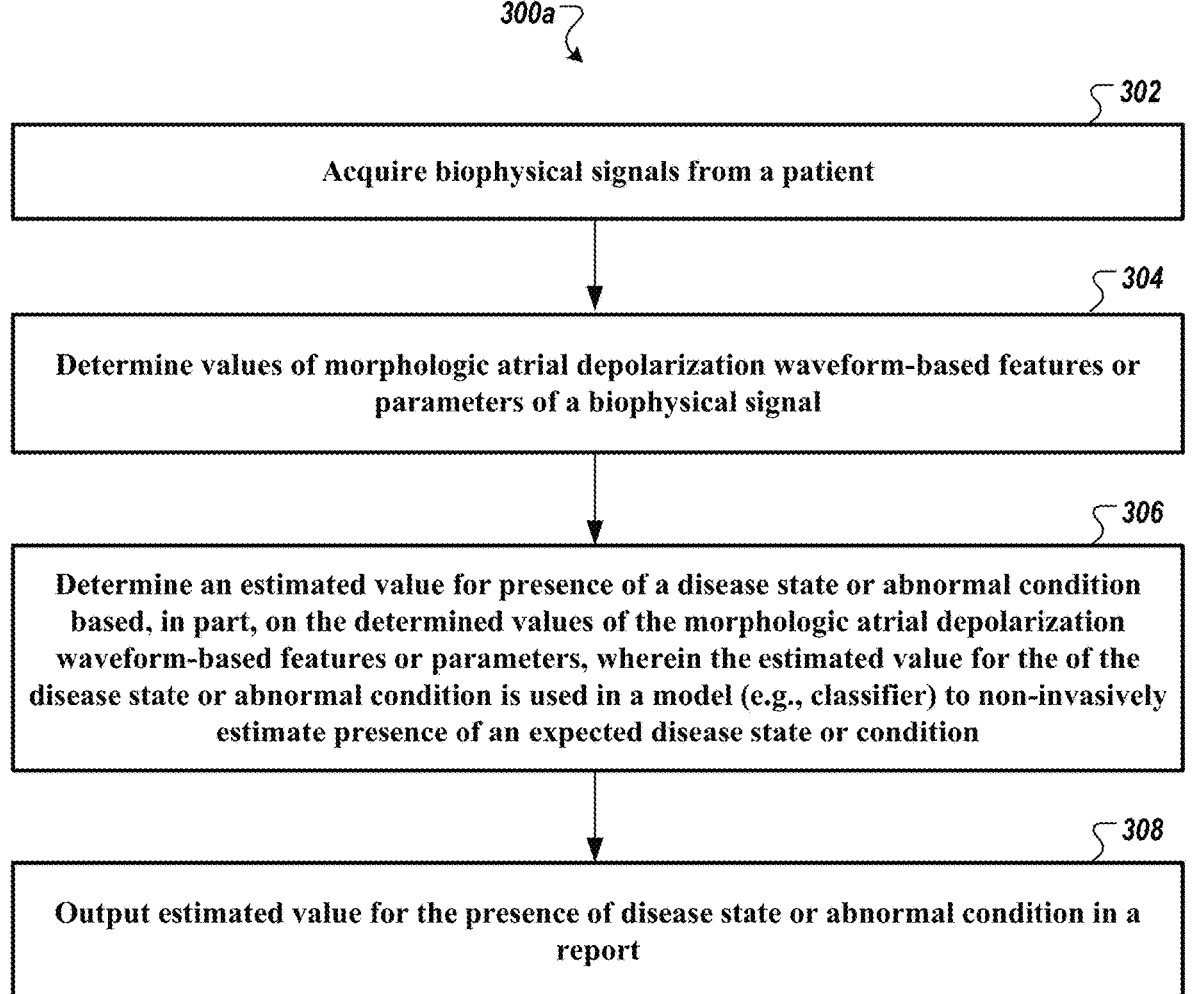

*300a*

*302*

Acquire biophysical signals from a patient

*304*

Determine values of morphologic atrial depolarization waveform-based features or parameters of a biophysical signal

*306*

Determine an estimated value for presence of a disease state or abnormal condition based, in part, on the determined values of the morphologic atrial depolarization waveform-based features or parameters, wherein the estimated value for the of the disease state or abnormal condition is used in a model (e.g., classifier) to non-invasively estimate presence of an expected disease state or condition

*308*

Output estimated value for the presence of disease state or abnormal condition in a report

Obtain biophysical signals from a subject

*312*

Determine morphologic atrial depolarization waveform-based features or parameters
from the acquired biophysical signals

*314*

Output the morphologic atrial depolarization waveform-based features or parameters

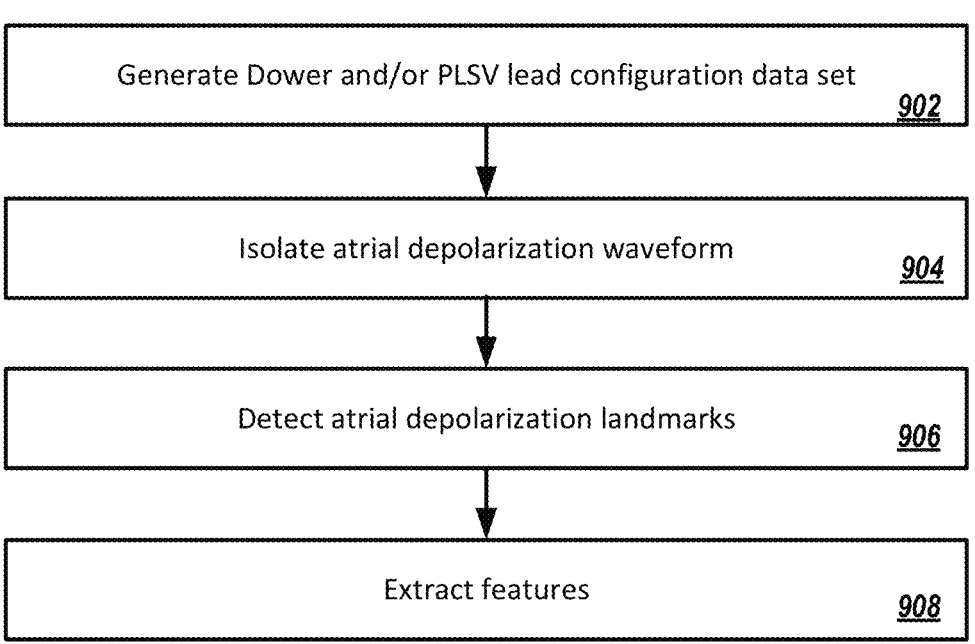

Generate Dower and/or PLSV lead configuration data set

*902*

Isolate atrial depolarization waveform

*904*

Detect atrial depolarization landmarks

*906*

Extract features

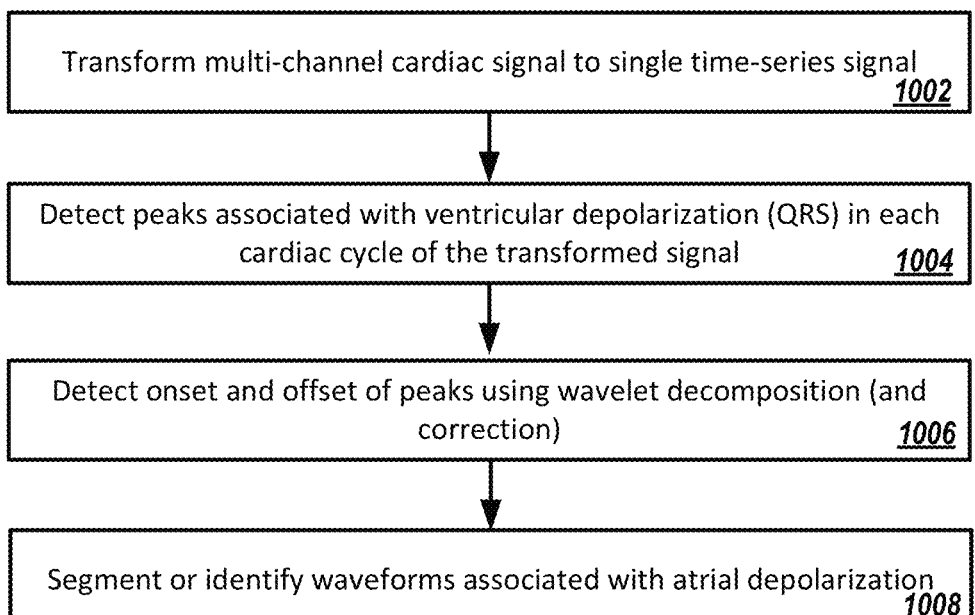

Transform multi-channel cardiac signal to single time-series signal

*1002*

Detect peaks associated with ventricular depolarization (QRS) in each cardiac cycle of the transformed signal

*1004*

Detect onset and offset of peaks using wavelet decomposition (and correction)

*1006*

Segment or identify waveforms associated with atrial depolarization

METHODS AND SYSTEMS FOR ENGINEERING CARDIAC WAVEFORM FEATURES FROM BIOPHYSICAL SIGNALS FOR USE IN CHARACTERIZING PHYSIOLOGICAL SYSTEMS

RELATED APPLICATION

This US application claims priority to, and the benefit of, U.S. Provisional Patent Application No. 63/236,193, filed Aug. 23, 2021, entitled "Methods and Systems for Engineering Cardiac Waveform Features From Biophysical Signals for Use in Characterizing Physiological Systems," which is incorporated by reference herein in its entirety.

FIELD OF THE INVENTIONS

The present disclosure generally relates to methods and systems for engineering features or parameters from biophysical signals for use in diagnostic applications; in particular, the engineering and use of morphologic atrial depolarization waveform-based features for use in characterizing one or more physiological systems and their associated functions, activities, and abnormalities. The features or parameters may also be used for monitoring or tracking, controls of medical equipment, or to guide the treatment of a disease, medical condition, or an indication of either.

BACKGROUND

There are numerous methods and systems for assisting a healthcare professional in diagnosing disease. Some of these involve the use of invasive or minimally invasive techniques, radiation, exercise or stress, or pharmacological agents, sometimes in combination, with their attendant risks and other disadvantages.

Diastolic heart failure, a major cause of morbidity and mortality, is defined as symptoms of heart failure in a patient with preserved left ventricular function. It is characterized by a stiff left ventricle with decreased compliance and impaired relaxation leading to increased end-diastolic pressure in the left ventricle, which is measured through left heart catheterization. Current clinical standard of care for diagnosing pulmonary hypertension (PH), and for pulmonary arterial hypertension (PAH), in particular, involves a cardiac catheterization of the right side of the heart that directly measures the pressure in the pulmonary arteries. Coronary angiography is the current standard of care used to assess coronary arterial disease (CAD) as determined through the coronary lesions described by a treating physician. Non-invasive imaging systems such as magnetic resonance imaging and computed tomography require specialized facilities to acquire images of blood flow and arterial blockages of a patient that are reviewed by radiologists.

It is desirable to have a system that can assist healthcare professionals in the diagnosis of cardiac disease and various other diseases and conditions without the aforementioned disadvantages.

SUMMARY

A clinical evaluation system and method are disclosed that facilitate the use of one or more morphologic atrial depolarization waveform-based features or parameters (also referred to herein as "morphologic features or parameters" or "physiological features or parameters") determined from biophysical signals such as cardiac or biopotential signals that are acquired, in preferred embodiments, non-invasively from surface sensors placed on a patient while the patient is at rest. Morphologic atrial depolarization waveform-based features or parameters can be used in a model or classifier (e.g., a machine-learned classifier) to estimate metrics associated with the physiological state of a patient, including for the presence or non-presence of a disease, medical condition, or an indication of either. The estimated metric may be used to assist a physician or other healthcare provider in diagnosing the presence or non-presence and/or severity and/or localization of diseases or conditions or in the treatment of said diseases or conditions. The estimation or determined likelihood of the presence or non-presence of a disease, condition, or indication of either can supplant, augment, or replace other evaluation or measurement modalities for the assessment of a disease or medical condition. In some cases, a determination can take the form of a numerical score and related information. Morphology of the atrial depolarization waveform can be distinctly different when comparing those of healthy atria and those of pathological atria. Left Atrial Enlargement (LAE), Right Atrial Enlargement (RAE), and Biatrial Enlargement (BAE) present as unique morphologies which can deviate from healthy and unhealthy people.

As used herein, the term "feature" (in the context of machine learning and pattern recognition and as used herein) generally refers to an individual measurable property or characteristic of a phenomenon being observed. A feature is defined by analysis and may be determined in groups in combination with other features from a common model or analytical framework.

As used herein, "metric" refers to an estimation or likelihood of the presence, non-presence, severity, and/or localization (where applicable) of one or more diseases, conditions, or indication(s) of either, in a physiological system or systems. Notably, the exemplified methods and systems can be used in certain embodiments described herein to acquire biophysical signals and/or to otherwise collect data from a patient and to evaluate those signals and/or data in signal processing and classifier operations to evaluate for a disease, condition, or indicator of one that can supplant, augment, or replace other evaluation modalities via one or more metrics. In some cases, a metric can take the form of a numerical score and related information.

As used herein, the terms "signal" and "waveform" are used interchangeably. A signal data set may include two or more signals or waveforms of similar (e.g., different channels from same or different acquisition devices) or different modalities (on integrated or separate acquisition devices).

In the context of cardiovascular and respiratory systems, examples of diseases and conditions to which such metrics can relate include, for example: (i) heart failure (e.g., left-side or right-side heart failure; heart failure with preserved ejection fraction (HFpEF)), (ii) coronary artery disease (CAD), (iii) various forms of pulmonary hypertension (PH) including without limitation pulmonary arterial hypertension (PAH), (iv) abnormal left ventricular ejection fraction (LVEF), and various other diseases or conditions. An example indicator of certain forms of heart failure is the presence or non-presence of elevated or abnormal left-ventricular end-diastolic pressure (LVEDP). An example indicator of certain forms of pulmonary hypertension is the presence or non-presence of elevated or abnormal mean pulmonary arterial pressure (mPAP).

BRIEF DESCRIPTION OF THE DRAWINGS

The accompanying drawings, which are incorporated in and constitute a part of this specification, illustrate embodiments and, together with the description, serve to explain the principles of the methods and systems.

Embodiments of the present invention may be better understood from the following detailed description when read in conjunction with the accompanying drawings. Such embodiments, which are for illustrative purposes only, depict novel and non-obvious aspects of the invention. The drawings include the following figures:

FIGS. 3-4 each shows an example method to use mor-phologic atrial depolarization waveform-based features or parameters or their intermediate data in a practical applica-tion for diagnostics, treatment, monitoring, or tracking in accordance with an illustrative embodiment.

FIGS. 9 and 10 each shows detailed implementation of the morphologic atrial depolarization waveform feature compu-tation module in accordance with an illustrative embodi-ment.

DETAILED DESCRIPTION

Figure 1:
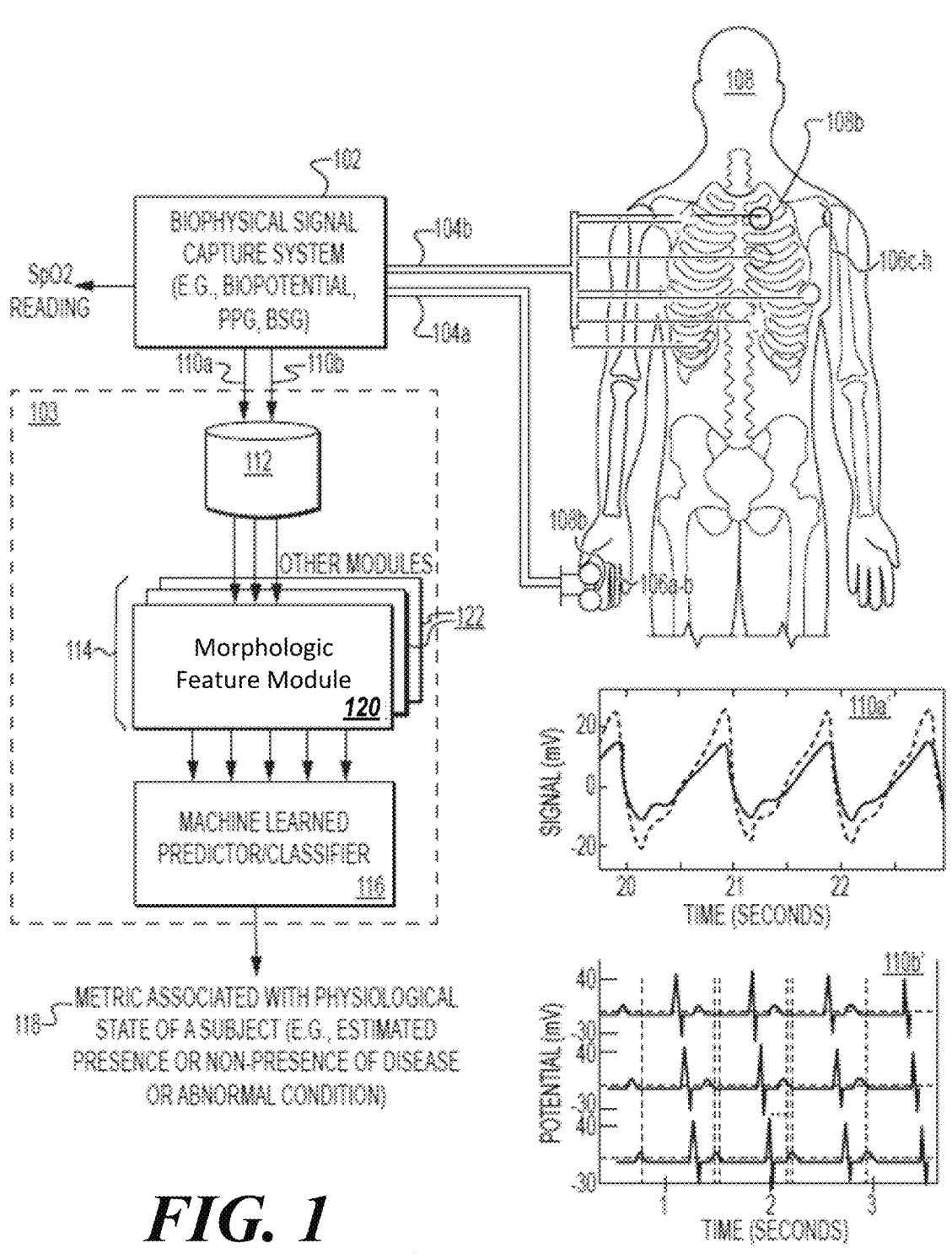
FIG. 1 is a schematic diagram of example modules, or components, configured to non-invasively compute morpho-logic atrial depolarization waveform-based features or parameters to generate one or more metrics associated with the physiological state of a patient in accordance with an illustrative embodiment.

Each and every feature described herein, and each and every combination of two or more of such features, is included within the scope of the present invention provided that the features included in such a combination are not mutually inconsistent.

While the present disclosure is directed to the practical assessment of biophysical signals, e.g., raw or pre-processed photoplethysmographic signals, biopotential/cardiac sig-nals, etc., in the diagnosis, tracking, and treatment of car-diac-related pathologies and conditions, such assessment can be applied to the diagnosis, tracking, and treatment (including without limitation surgical, minimally invasive, lifestyle, nutritional, and/or pharmacologic treatment, etc.) of any pathologies or conditions in which a biophysical signal is involved in any relevant system of a living body. The assessment may be used in the controls of medical equipment or wearable devices or in monitoring applications (e.g., to report the PPG waveform-based features, param-eters, or an intermediate output discussed herein)

The terms "subject" and "patient" as used herein are generally used interchangeably to refer to those who had undergone analysis performed by the exemplary systems and methods.

The term "cardiac signal" as used herein refers to one or more signals directly or indirectly associated with the struc-ture, function, and/or activity of the cardiovascular system—including aspects of that signal's electrical/electrochemical conduction—that, e.g., cause contraction of the myocar-dium. A cardiac signal may include, in some embodiments, biopotential signals or electrocardiographic signals, e.g., those acquired via an electrocardiogram (ECG), the cardiac and photoplethysmographic waveform or signal capture or recording instrument later described herein, or other modali-ties.

The term "biophysical signal" as used herein includes but is not limited to one or more cardiac signal(s), neurological signal(s), ballistocardiographic signal(s), and/or photopl-ethysmographic signal(s), but it also encompasses more broadly any physiological signal from which information may be obtained. Not intending to be limited by example, one may classify biophysical signals into types or categories that can include, for example, electrical (e.g., certain cardiac and neurological system-related signals that can be observed, identified, and/or quantified by techniques such as the measurement of voltage/potential (e.g., biopotential), impedance, resistivity, conductivity, current, etc. in various domains such as time and/or frequency), magnetic, electro-magnetic, optical (e.g., signals that can be observed, iden-tified and/or quantified by techniques such as reflectance, interferometry, spectroscopy, absorbance, transmissivity, visual observation, photoplethysmography, and the like), acoustic, chemical, mechanical (e.g., signals related to fluid flow, pressure, motion, vibration, displacement, strain), ther-mal, and electrochemical (e.g., signals that can be correlated to the presence of certain analytes, such as glucose). Bio-physical signals may in some cases be described in the context of a physiological system (e.g., respiratory, circula-tory (cardiovascular, pulmonary), nervous, lymphatic, endo-crine, digestive, excretory, muscular, skeletal, renal/urinary/excretory, immune, integumentary/exocrine and reproductive systems), one or more organ system(s) (e.g., signals that may be unique to the heart and lungs as they work together), or in the context of tissue (e.g., muscle, fat, nerves, connective tissue, bone), cells, organelles, molecules (e.g., water, proteins, fats, carbohydrates, gases, free radi-cals, inorganic ions, minerals, acids, and other compounds, elements, and their subatomic components. Unless stated otherwise, the term "biophysical signal acquisition" gener-ally refers to any passive or active means of acquiring a biophysical signal from a physiological system, such as a mammalian or non-mammalian organism. Passive and active biophysical signal acquisition generally refers to the observation of natural or induced electrical, magnetic, optical, and/or acoustics emittance of the body tissue. Non-limiting examples of passive and active biophysical signal acquisition means include, e.g., voltage/potential, current, magnetic, optical, acoustic, and other non-active ways of observing the natural emittance of the body tissue, and in some instances, inducing such emittance. Non-limiting examples of passive and active biophysical signal acquisition means include, e.g., ultrasound, radio waves, microwaves, infrared and/or visible light (e.g., for use in pulse oximetry or photoplethysmography), visible light, ultraviolet light, and other ways of actively interrogating the body tissue that does not involve ionizing energy or radiation (e.g., X-ray). An active biophysical signal acquisition may involve excitation-emission spectroscopy (including, for example, excitation-emission fluorescence). The active biophysical signal acquisition may also involve transmitting ionizing energy or radiation (e.g., X-ray) (also referred to as "ionizing biophysical signal") to the body tissue. Passive and active biophysical signal acquisition means can be performed in conjunction with invasive procedures (e.g., via surgery or invasive radiologic intervention protocols) or non-invasively (e.g., via imaging, ablation, heart contraction regulation (e.g., via pacemakers), catheterization, etc.).

The term "photoplethysmographic signal" as used herein refers to one or more signals or waveforms acquired from optical sensors that correspond to measured changes in light absorption by oxygenated and deoxygenated hemoglobin, such as light having wavelengths in the red and infrared spectra. Photoplethysmographic signal(s), in some embodiments, include a raw signal(s) acquired via a pulse oximeter or a photoplethysmogram (PPG). In some embodiments, photoplethysmographic signal(s) are acquired from off-the-shelf, custom, and/or dedicated equipment or circuitries that are configured to acquire such signal waveforms for the purpose of monitoring health and/or diagnosing disease or abnormal conditions. The photoplethysmographic signal(s) typically include a red photoplethysmographic signal (e.g., an electromagnetic signal in the visible light spectrum most dominantly having a wavelength of approximately 625 to 740 nanometers) and an infrared photoplethysmographic signal (e.g., an electromagnetic signal extending from the nominal red edge of the visible spectrum up to about 1 mm), though other spectra such as near-infrared, blue and green may be used in different combinations, depending on the type and/or mode of PPG being employed.

The term "ballistocardiographic signal," as used herein, refers to a signal or group of signals that generally reflect the flow of blood through the entire body that may be observed through vibration, acoustic, movement, or orientation. In some embodiments, ballistocardiographic signals are acquired by wearable devices, such as vibration, acoustic, movement, or orientation-based seismocardiogram (SCG) sensors, which can measure the body's vibrations or orientation as recorded by sensors mounted close to the heart. Seismocardiogram sensors are generally used to acquire "seismocardiogram," which is used interchangeably with the term "ballistocardiogram" herein. In other embodiments, ballistocardiographic signals may be acquired by external equipment, e.g., bed or surface-based equipment that measures phenomena such as a change in body weight as blood moves back and forth in the longitudinal direction between the head and feet. In such embodiments, the volume of blood in each location may change dynamically and be reflected in the weight measured at each location on the bed as well as the rate of change of that weight.

In addition, the methods and systems described in the various embodiments herein are not so limited and may be utilized in any context of another physiological system or systems, organs, tissue, cells, etc., of a living body. By way of example only, two biophysical signal types that may be useful in the cardiovascular context include cardiac/biopotential signals that may be acquired via conventional electrocardiogram (ECG/EKG) equipment, bipolar wide-band biopotential (cardiac) signals that may be acquired from other equipment such as those described herein, and signals that may be acquired by various plethysmographic techniques, such as, e.g., photoplethysmography. In another example, the two biophysical signal types can be further augmented by ballistocardiographic techniques.

FIG. 1 is a schematic diagram of example modules, or components, configured to non-invasively compute morphologic atrial depolarization waveform-based features or parameters to generate, via a classifier (e.g., machine-learned classifier), one or more metrics associated with the physiological state of a patient in accordance with an illustrative embodiment. The modules or components may be used in a production application or the development of the morphologic atrial depolarization waveform-based features and other classes of features.

The example analysis and classifiers described herein may be used to assist a healthcare provider in the diagnosis and/or treatment of cardiac- and cardiopulmonary-related pathologies and medical conditions, or an indicator of one. Examples include significant coronary artery disease (CAD), one or more forms of heart failure such as, e.g., heart failure with preserved ejection fraction (HFpEF), congestive heart failure, various forms of arrhythmia, valve failure, various forms of pulmonary hypertension, among various other disease and conditions disclosed herein.

In addition, there exist possible indicators of a disease or condition, such as an elevated or abnormal left ventricular end-diastolic pressure (LVEDP) value as it relates to some forms of heart failure, abnormal left ventricular ejection fraction (LVEF) values as they relate to some forms of heart failure or an elevated mean pulmonary arterial pressure (mPAP) value as it relates to pulmonary hypertension and/or pulmonary arterial hypertension. Indicators of the likelihood that such indicators are abnormal/elevated or normal, such as those provided by the example analysis and classifiers described herein, can help a healthcare provider assess or diagnose that the patient has or does not have a given disease or condition. In addition to these metrics associated with a disease state of condition, other measurements and factors may be employed by a healthcare professional in making a diagnosis, such as the results of a physical examination and/or other tests, the patient's medical history, current medications, etc. The determination of the presence or non-presence of a disease state or medical condition can include the indication (or a metric of measure that is used in the diagnosis) for such disease.

In FIG. 1, the components include at least one non-invasive biophysical signal recorder or capture system 102 and an assessment system 103 that is located, for example, in a cloud or remote infrastructure or in a local system. Biophysical signal capture system 102 (also referred to as a biophysical signal recorder system), in this embodiment, is configured to, e.g., acquire, process, store and transmit synchronously acquired patient's electrical and hemodynamic signals as one or more types of biophysical signals 104. In the example of FIG. 1, the biophysical signal capture system 102 is configured to synchronously capture two types of biophysical signals shown as first biophysical signals 104a (e.g., synchronously acquired to other first biophysical signals) and second biophysical signals 104b (e.g., synchronously acquired to the other biophysical signals) acquired from measurement probes 106 (e.g., shown as probes 106a and 106b, e.g., comprising hemodynamic sensors for hemodynamic signals 104a, and probes 106c-106h comprising leads for electrical/cardiac signals 104b). The probes 106a-h are placed on, e.g., by being adhered to or placed next to, a surface tissue of a patient 108 (shown at patient locations 108a and 108b). The patient is preferably a human patient, but it can be any mammalian patient. The acquired raw biophysical signals (e.g., 106a and 106b) together form a biophysical-signal data set 110 (shown in FIG. 1 as a first biophysical-signal data set 110a and a second biophysical-signal data set 110b, respectively) that may be stored, e.g., as a single file, preferably, that is identifiable by a recording/signal captured number and/or by a patient's name and medical record number.

In the FIG. 1 embodiment, the first biophysical-signal data set 110a comprises a set of raw photoplethysmographic, or hemodynamic, signal(s) associated with measured changes in light absorption of oxygenated and/or deoxygenated hemoglobin from the patient at location 108a, and the second biophysical-signal data set 110b comprises a set of raw cardiac or biopotential signal(s) associated with electrical signals of the heart. Though in FIG. 1, raw photoplethysmographic or hemodynamic signal(s) are shown being acquired at a patient's finger, the signals may be alternatively acquired at the patient's toe, wrist, forehead, earlobe, neck, etc. Similarly, although the cardiac or biopotential signal(s) are shown to be acquired via three sets of orthogonal leads, other lead configurations may be used (e.g., 11 lead configuration, 12 lead configuration, etc.).

Plots 110a' and 110b' show examples of the first biophysical-signal data set 110a and the second biophysical-signal data set 110a, respectively. Specifically, Plot 110a' shows an example of an acquired photoplethysmographic or hemodynamic signal. In Plot 110a', the photoplethysmographic signal is a time series signal having a signal voltage potential as a function of time as acquired from two light sources (e.g., infrared and red-light source). Plot 110b' shows an example cardiac signal comprising a 3-channel potential time series plot. In some embodiments, the biophysical signal capture system 102 preferably acquires biophysical signals via non-invasive means or component(s). In alternative embodiments, invasive or minimally-invasively means or component(s) may be used to supplement or as substitutes for the non-invasive means (e.g., implanted pressure sensors, chemical sensors, accelerometers, and the like). In still further alternative embodiments, non-invasive and non-contact probes or sensors capable of collecting biophysical signals may be used to supplement or as substitutes for the non-invasive and/or invasive/minimally invasive means, in any combination (e.g., passive thermometers, scanners, cameras, x-ray, magnetic, or other means of non-contact or contact energy data collection system as discussed herein). Subsequent to signal acquisitions and recording, the biophysical signal capture system 102 then provides, e.g., sending over a wireless or wired communication system and/or a network, the acquired biophysical-signal data set 110 (or a data set derived or processed therefrom, e.g., filtered or pre-processed data) to a data repository 112 (e.g., a cloud-based storage area network) of the assessment system 103. In some embodiments, the acquired biophysical-signal data set 110 is sent directly to the assessment system 103 for analysis or is uploaded to a data repository 112 through a secure clinician's portal.

Biophysical signal capture system 102 is configured with circuitries and computing hardware, software, firmware, middleware, etc., in some embodiments, to acquire, store, transmit, and optionally process both the captured biophysical signals to generate the biophysical-signal data set 110. An example biophysical signal capture system 102 and the acquired biophysical-signal set data 110 are described in U.S. Pat. No. 10,542,898, entitled "Method and Apparatus for Wide-Band Phase Gradient Signal Acquisition," or U.S. Patent Publication No. 2018/0249960, entitled "Method and Apparatus for Wide-Band Phase Gradient Signal Acquisition," each of which is hereby incorporated by reference herein in its entirety.

In some embodiments, biophysical signal capture system 102 includes two or more signal acquisition components, including a first signal acquisition component (not shown) to acquire the first biophysical signals (e.g., photoplethysmographic signals) and includes a second signal acquisition component (not shown) to acquire the second biophysical signals (e.g., cardiac signals). In some embodiments, the electrical signals are acquired at a multi-kilohertz rate for a few minutes, e.g., between 1 kHz and 10 kHz. In other embodiments, the electrical signals are acquired between 10 kHz and 100 kHz. The hemodynamic signals may be acquired, e.g., between 100 Hz and 1 kHz.

Biophysical signal capture system 102 may include one or more other signal acquisition components (e.g., sensors such as mechano-acoustic, ballistographic, ballistocardiographic, etc.) for acquiring signals. In other embodiments of the signal capture system 102, a signal acquisition component comprises conventional electrocardiogram (ECG/EKG) equipment (e.g., Holter device, 12 lead ECG, etc.).

Figure 12A:
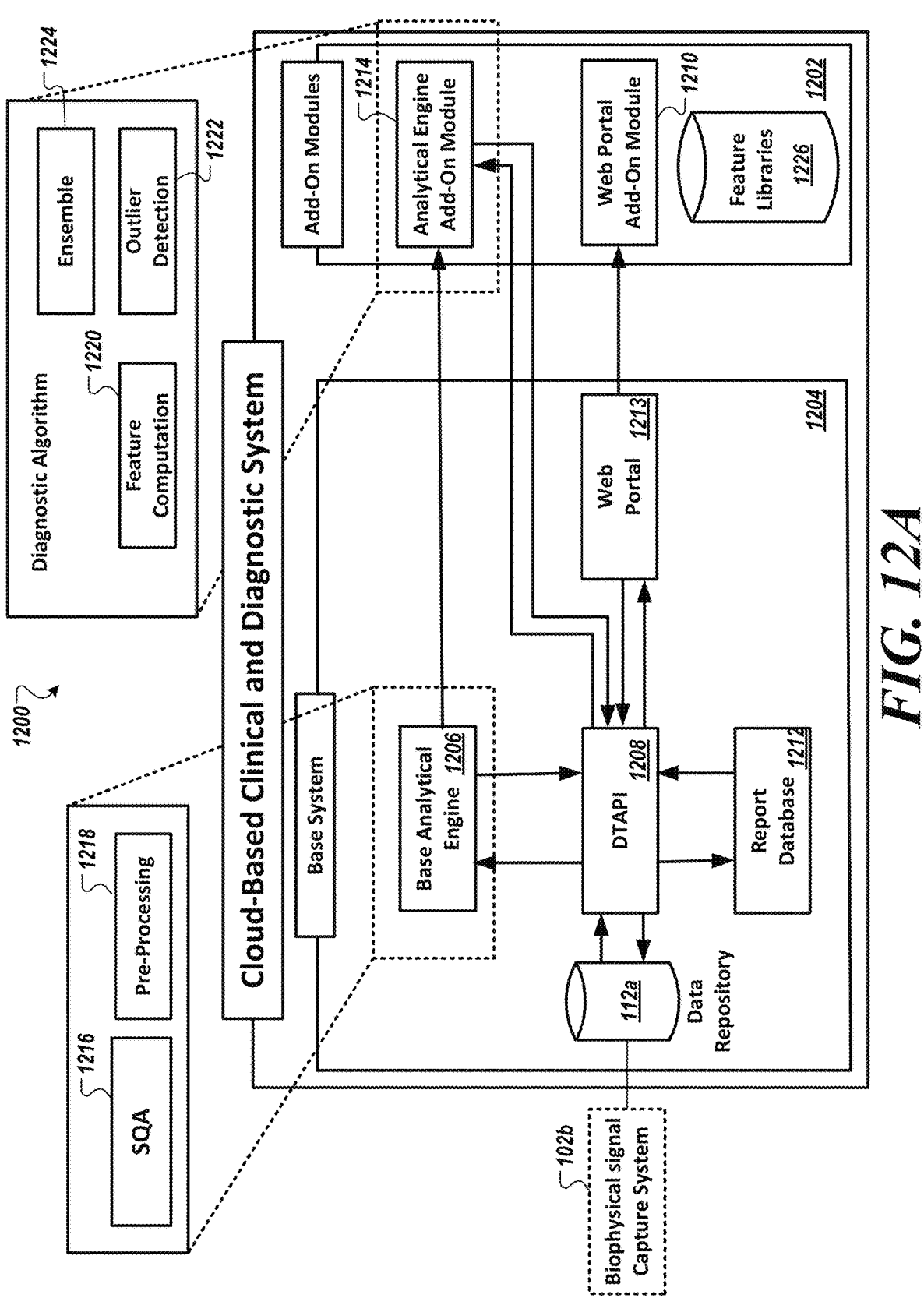
FIG. 12A shows a schematic diagram of an example clinical evaluation system configured to use morphologic atrial depolarization waveform-based features or parameters among other computed features to generate one or more metrics associated with the physiological state of a patient in accordance with an illustrative embodiment.
Figure 12B:
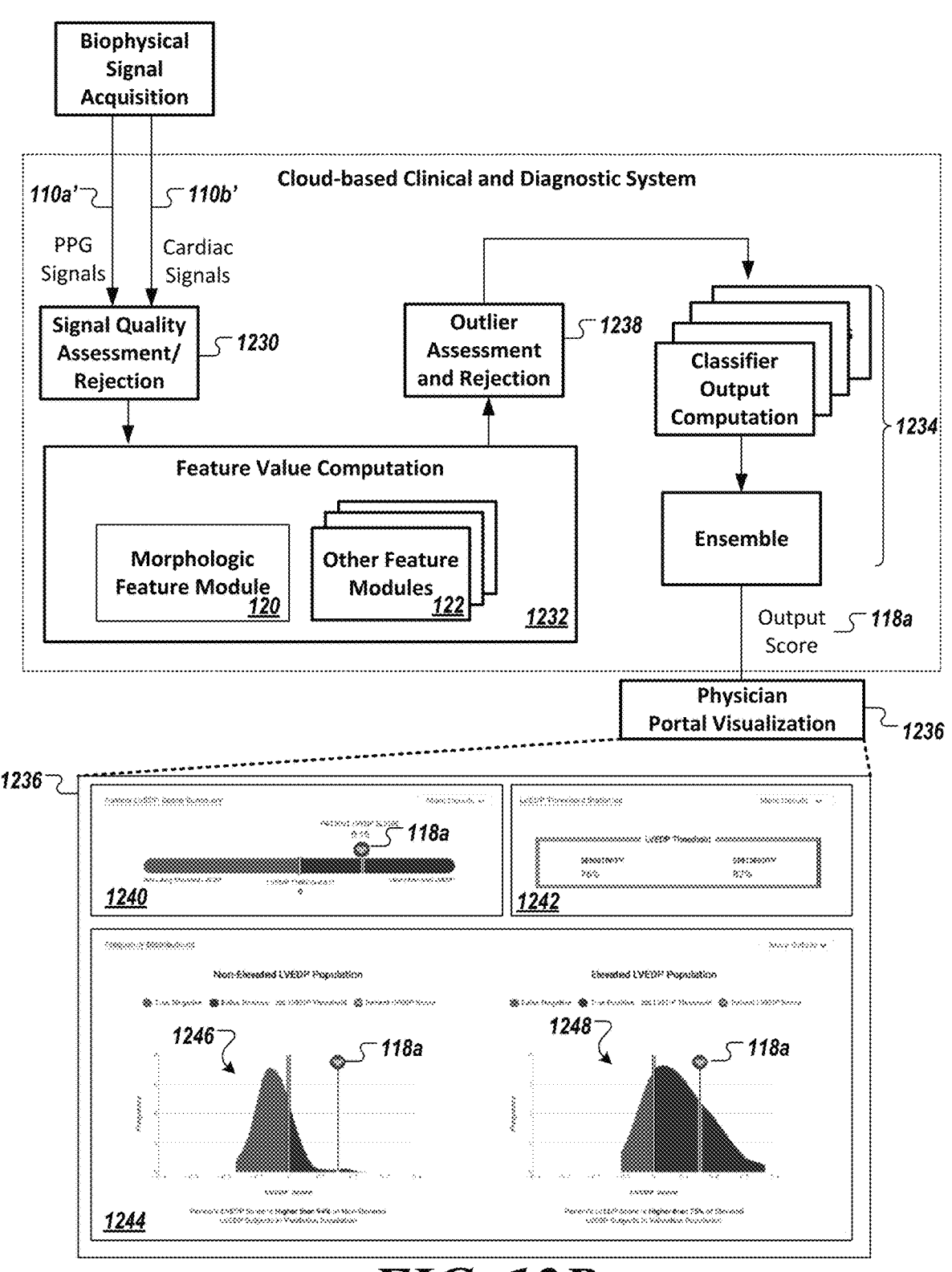
FIG. 12B shows a schematic diagram of the operation of the example clinical evaluation system of FIG. 12A in accordance with an illustrative embodiment.

Assessment system 103 comprises, in some embodiments, the data repository 112 and an analytical engine or analyzer (not shown—see FIGS. 12A and 12B). Assessment system 103 may include feature modules 114 and a classifier module 116 (e.g., an ML classifier module). In FIG. 1, Assessment system 103 is configured to retrieve the acquired biophysical signal data set 110, e.g., from the data repository 112, and use it in the feature modules 114, which is shown in FIG. 1 to include a morphologic atrial depolarization waveform feature module 120 (shown as "Morphologic Feature Module" 120) and other modules 122 (later described herein). The features modules 114 compute values of features or parameters, including those of morphological atrial depolarization waveform-based features to provide to the classifier module 116, which computes an output 118, e.g., an output score, of the metrics associated with the physiological state of a patient (e.g., an indication of the presence or non-presence of a disease state, medical condition, or an indication of either). Output 118 is subsequently presented, in some embodiments, at a healthcare physician portal (not shown—see FIGS. 12A and 12B) to be used by healthcare professionals for the diagnosis and treatment of pathology or a medical condition. In some embodiments, a portal may be configured (e.g., tailored) for access by, e.g., patient, caregivers, researchers, etc., with output 118 configured for the portal's intended audience. Other data and information may also be a part of output 118 (e.g., the acquired biophysical signals or other patient's information and medical history).

Classifier module 116 (e.g., ML classifier module) may include transfer functions, loop up tables, models, or operators developed based on algorithms such as but not limited to decision trees, random forests, neural networks, linear models, Gaussian processes, nearest neighbor, SVMs, Naïve Bayes, etc. In some embodiments, classifier module 116 may include models that are developed based on ML techniques described in U.S. Provisional Patent Application No. 63/235,960, filed Aug. 23, 2021, entitled "Method and System to Non-Invasively Assess Elevated Left Ventricular End-Diastolic Pressure"; U.S. Patent Publication No. 20190026430, entitled "Discovering Novel Features to Use in Machine Learning Techniques, such as Machine Learning Techniques for Diagnosing Medical Conditions"; or U.S. Patent Publication No. 20190026431, entitled "Discovering Genomes to Use in Machine Learning Techniques," each of which is hereby incorporated by reference herein in its entirety.

Example Biophysical Signal Acquisition.

Figure 2:
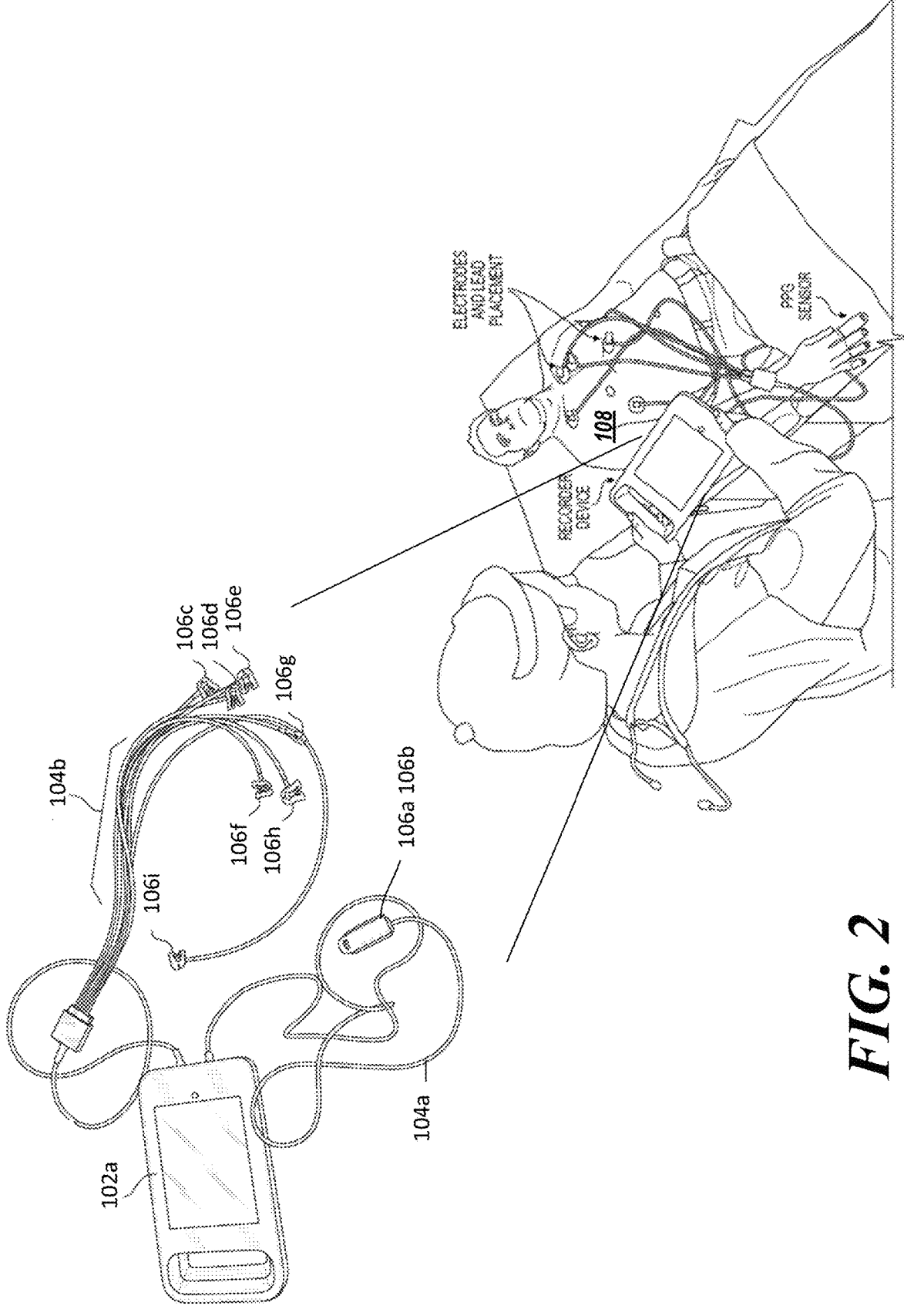
FIG. 2 shows an example biophysical signal capture system or component and its use in non-invasively collect-ing biophysical signals of a patient in a clinical setting in accordance with an illustrative embodiment.

FIG. 2 shows a biophysical signal capture system 102 (shown as 102a) and its use in non-invasively collecting biophysical signals of a patient in a clinical setting in accordance with an illustrative embodiment. In FIG. 2, the biophysical signal capture system 102a is configured to capture two types of biophysical signals from the patient 108 while the patient is at rest. The biophysical signal capture system 102a synchronously acquires the patient's (i) electrical signals (e.g., cardiac signals corresponding to the second biophysical-signal data set 110b) from the torso using orthogonally placed sensors (106c-106h; 106i is a $7^{th}$ common-mode reference lead) and (ii) hemodynamic signals (e.g., PPG signals corresponding to the first biophysical-signal data set 110a) from the finger using a photoplethysmographic sensor (e.g., collecting signals 106a, 106b).

As shown in FIG. 2, the electrical and hemodynamic signals (e.g., 104a, 104b) are passively collected via commercially available sensors applied to the patient's skin. The signals may be acquired beneficially without patient exposure to ionizing radiation or radiological contrast agents and without patient exercise or the use of pharmacologic stressors. The biophysical signal capture system 102a can be used in any setting conducive for a healthcare professional, such as a technician or nurse, to acquire the requisite data and where a cellular signal or Wi-Fi connection can be established.

The electrical signals (e.g., corresponding to the second biophysical signal data set 110b) are collected using three orthogonally paired surface electrodes arranged across the patient's chest and back along with a reference lead. The electrical signals are acquired, in some embodiments, using a low-pass anti-aliasing filter (e.g., ~2 kHz) at a multi-kilohertz rate (e.g., 8 thousand samples per second for each of the six channels) for a few minutes (e.g., 215 seconds). In alternative embodiments, the biophysical signals may be continuously/intermittently acquired for monitoring, and portions of the acquired signals are used for analysis. The hemodynamic signals (e.g., corresponding to the first biophysical signal data set 110a) are collected using a photoplethysmographic sensor placed on a finger. The photo-absorption of red light (e.g., any wavelengths between 600-750 nm) and infrared light (e.g., any wavelengths between 850-950 nm) are recorded, in some embodiments, at a rate of 500 samples per second over the same period. The biophysical signal capture system 102a may include a common mode drive that reduces common-mode environmental noise in the signal. The photoplethysmographic and cardiac signals were simultaneously acquired for each patient. Jitter (inter-modality jitter) in the data may be less than about 10 microseconds (μs). Jitter among the cardiac signal channels may be less than 10 microseconds, e.g., around ten femtoseconds (fs).

A signal data package containing the patient metadata and signal data may be compiled at the completion of the signal acquisition procedure. This data package may be encrypted before the biophysical signal capture system 102a transferring the package to the data repository 112. In some embodiments, the data package is transferred to the assessment system (e.g., 103). The transfer is initiated, in some embodiments, following the completion of the signal acquisition procedure without any user intervention. The data repository 112 is hosted, in some embodiments, on a cloud storage service that can provide secure, redundant, cloud-based storage for the patient's data packages, e.g., Amazon Simple Storage Service (i.e., "Amazon S3"). The biophysical signal capture system 102a also provides an interface for the practitioner to receive notification of an improper signal acquisition to alert the practitioner to immediately acquire additional data from the patient.

Example Method of Operation

Figure 4:
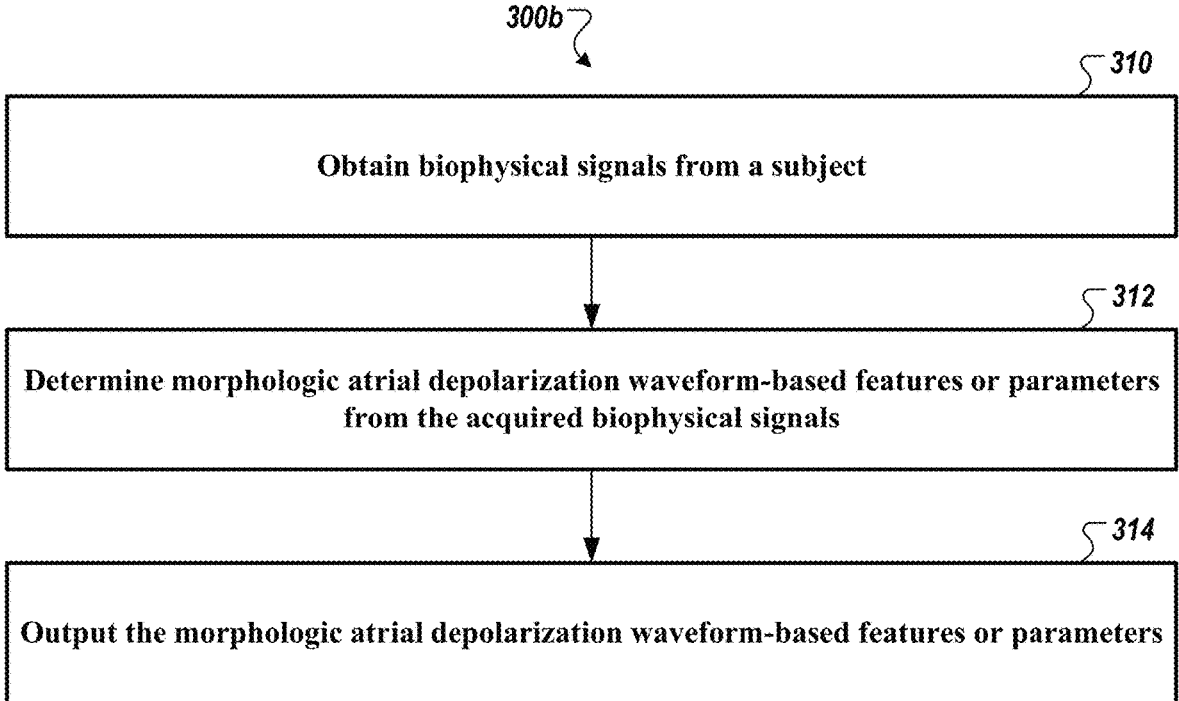

FIGS. 3 and 4 each shows an example method to use morphologic atrial depolarization waveform-based features or parameters or their intermediate outputs in a practical application for diagnostics, treatment, monitoring, or tracking.

Estimation of Presence of Disease State or Indicating Condition. FIG. 3 shows a method 300a that employs morphologic atrial depolarization waveform-based parameters or features to determine estimators of the presence of a disease state, medical condition, or indication of either, e.g., to aid in the diagnosis, tracking, or treatment. Method 300a includes the step of acquiring (302) biophysical signals from a patient (e.g., cardiac signals, photoplethysmographic signals, ballistocardiographic signals), e.g., as described in relation to FIGS. 1 and 2 and other examples as described herein. In some embodiments, the acquired biophysical signals are transmitted for remote storage and analysis. In other embodiments, the acquired biophysical signals are stored and analyzed locally.

As stated above, one example in the cardiac context is the estimation of the presence of abnormal left-ventricular end-diastolic pressure (LVEDP) or mean pulmonary artery pressure (mPAP), significant coronary artery disease (CAD), abnormal left ventricular ejection fraction (LVEF), and one or more forms of pulmonary hypertension (PH), such as pulmonary arterial hypertension (PAH). Other pathologies or indicating conditions that may be estimated include, e.g., one or more forms of heart failure such as, e.g., heart failure with preserved ejection fraction (HFpEF), arrhythmia, congestive heart failure, valve failure, among various other disease and medical conditions disclosed herein.

Method 300a further includes the step of retrieving (304) the data set and determining values of morphologic atrial depolarization waveform-based features or parameters. Example operations to determine the values of morphologic atrial depolarization waveform-based features or parameters are provided in relation to FIGS. 5-11 later discussed herein. Method 300a further includes the step of determining (306) an estimated value for a presence of a disease state, medical condition, or an indication of either based on an application of the determined morphologic atrial depolarization waveform-based features to an estimation model (e.g., ML models). An example implementation is provided in relation to FIGS. 12A and 12B.

Method 300a further includes the step of outputting (308) estimated value(s) for the presence of disease state or abnormal condition in a report (e.g., to be used diagnosis or treatment of the disease state, medical condition, or indication of either), e.g., as described in relation to FIGS. 1, 15A, and 15B and other examples described herein.

Diagnostics or Condition Monitoring or Tracking using Morphologic Atrial Depolarization Waveform-based Features. FIG. 4 shows a method 300b that employs morphologic atrial depolarization waveform-based features or parameters for monitoring or controls of medical equipment or health monitoring device. Method 300b includes the step of obtaining (302) biophysical signals from a patient (e.g., cardiac signals, photoplethysmographic signals, ballistocardiographic signals, etc.). The operation may be performed continuously or intermittently, e.g., to provide output for a report or as controls for the medical equipment or the health monitoring device.

Method 300b further includes determining (310) morphologic atrial depolarization waveform-based features or parameters from the acquired biophysical data set, e.g., as described in relation to FIGS. 5-11. The determination based may be based on analysis of the continuously acquired signals over a moving-window.

The method 300b further includes outputting (312) morphologic atrial depolarization waveform-based features or parameters (e.g., in a report for use in diagnostics or as signals for controls). For monitoring and tracking, the output may be via a wearable device, a handheld device, or medical diagnostic equipment (e.g., pulse oximeter system, wearable health monitoring systems) to provide augmented data associated with health. In some embodiments, the outputs may be used in resuscitation systems, cardiac or pulmonary stress test equipment, pacemakers.

Morphologic Atrial Depolarization Waveform Features

The exemplary method and system are configured to assess properties of the shapes of atrial depolarization waveforms and to identify the presence or non-presence of atrial enlargement characteristics within the waveforms.

The morphology of the atrial depolarization waveforms can be distinctly different when comparing those of healthy atria with those of pathological atria. Left Atrial Enlargement (LAE), Right Atrial Enlargement (RAE), and Bi-atrial Enlargement (BAE) can provide manifest themselves with unique waveform morphologies that can be assessed as features or parameters. Healthy atria in Dower-transformed lead II or PLSV-transformed lead II generally have a monophasic morphology, meaning that there is a single positive peak where both atria contract in unison. Two peaks can be observed as the atria shift away from unity. The morphology of a wave with two positive peaks is generally referred to as "bifid." Healthy atria in Dower-transformed lead V1 or PLSV-transformed lead V1 generally have a balanced biphasic morphology, such that there is a balance in terms of duration and amplitude between the initial convex portion and the terminal concave portion. Atrial enlargement can cause a shift in this balance, and the amplitude can increase during the initial, terminal, or both portions.

Figure 5:
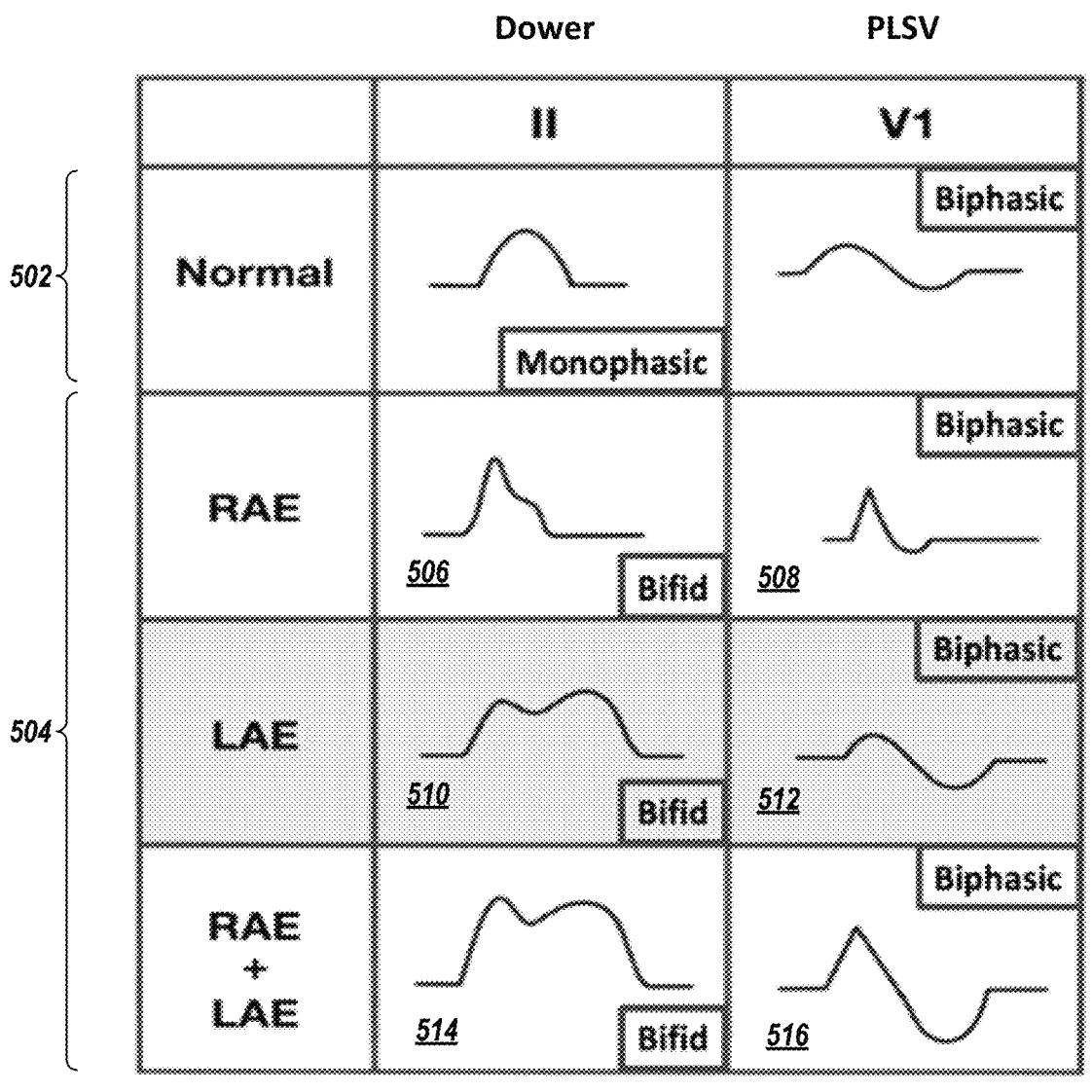
FIG. 5 is a diagram showing balanced or symmetric monophasic and bifid morphologies of atrial depolarization and imbalanced and asymmetric monophasic and bifid mor-phologies of atrial depolarization in accordance with an illustrative embodiment.

FIG. 5 is a diagram showing balanced or symmetric atrial depolarization with monophasic and bifid morphologies 502 and imbalanced and asymmetric atrial depolarization with monophasic and bifid morphologies 504 in accordance with an illustrative embodiment. In FIG. 5, unbalanced and asymmetric morphologies associated with Left Atrial Enlargement (LAE_II and LAE_V1) (506, 508), Right Atrial Enlargement (RAE_II and RAE_V1) (510, 512), and Bi-atrial Enlargement (BAE_II and BAE_VI) (514, 516) are shown, and they indicated morphologies in the waveform that are indicative of pathological atria. Specifically, left or right atrial enlargement, indicative of a cardiac pathology, has been correlated to certain unbalanced or unbalanced waveform morphologies.

Physiological Features Computation Modules

Figure 6:
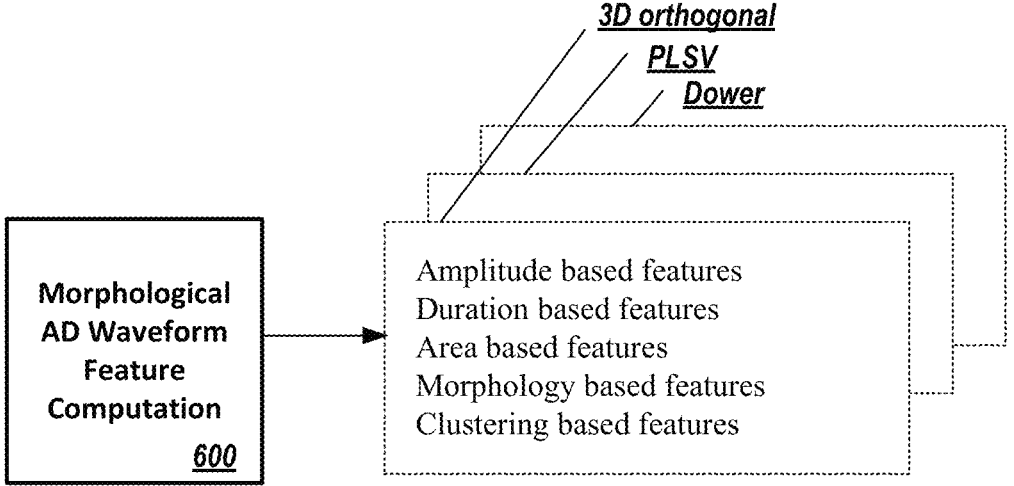
FIG. 6 illustrates an example morphologic atrial depolar-ization waveform feature computation module in accor-dance with an illustrative embodiment.

FIG. 6 shows an example physiological-related feature computation module, for a total of two example modules, configured to determine values of physiological features or parameters in accordance with an illustrative embodiment. In particular, FIG. 6 shows a morphologic atrial depolarization feature computation module 600 that can determine features or parameters associated with abnormal atrial depolarization from an acquired biopotential/cardiac signal. The assessment module 103, more specifically the analytical engine or analyzer therein, may call on specific feature functions within any of these module 600 in whole or in part as described below for a given clinical application.

Morphologic Atrial Depolarization Features

FIG. 6 illustrates, as a feature or parameter category, an example morphologic atrial depolarization feature computation module 600 configured to assess for the presence of Left Atrial Enlargement (LAE), Right Atrial Enlargement (RAE), and Biatrial Enlargement (BAE) waveforms that are indicating of pathological atria. In particular, Module 600 can isolate or delineate atrial depolarization waveforms in the three orthogonal lead configurations (e.g., a Frank lead configuration) and 12-lead ECG lead configuration (e.g., using the Dower transform or PLSV transform) to assess for waveform morphologies associated with Left Atrial Enlargement (LAE_II, LAE_V1) or Biatrial Enlargement (BAE_II, BAE_V1) and compute features or parameters based on these waveform morphologies. To assess the waveform, Module 600 can determine fiducial points in the atrial depolarization waveforms and determine features such as waveform amplitudes, waveform durations, and shape using the fiducial points. In the example of FIG. 6, these features or parameters include the amplitude of peaks in the isolated waveform, their duration, waveform area, and/or the presence of Left Atrial Enlargement (LAE_II, LAE_V1) or Biatrial Enlargement (BAE_II, BAE_V1) in Dower-transformed leads I, II, V1 or PLSV-transformed leads I, II, V1.

Table 1 shows a summarized list of 15 extractable morphologic atrial depolarization features that can be generated for a 3-orthogonal lead configuration, Dower-transformed leads I, II, VI, and PLSV-transformed leads I, II, V1. The 15 feature types can be characterized in 4 categories: amplitude-based, duration-based, area-based, and waveform shape-based (e.g., as described in relation to FIG. 6). The 2 amplitude-based features, 2 duration-based features, and 4 area-based features (Table 1) can be computed for each or some of the Dower or PLSV transformed leads I, II, V1 and the 3 lead orthogonal waveforms to provide up to a total of 36 features. The 4 atrial enlargement features (LAE_II, LAE_V1, BAE_II, BAE_V1), the morphology shape feature, and the morphology index feature, for a total of 6 feature types (Table 1), can be determined for 9 leads, namely, Dower-transformed leads I, II, and V1, PLSV-transformed leads I, II, and V1, and leads X, Y, and Z of the 3-lead orthogonal waveform to provide up to a total of 54 features (continuous output). The 4 atrial enlargement features (LAE_II, LAE_V1, BAE_II, BAE_V1) can include a binary output for the Dower-transformed leads II and VI and the PLSV-transformed leads II and VI to provide up to additional 16 features. Binary definitions for atrial enlargement with respect to the three-orthogonal lead configuration are not necessary. The 4 atrial enlargement features (LAE_II, LAE_V1, BAE_II, BAE_V1) and morphology and index features (6 total) can be further assessed with respect to gender groups (e.g., male, female, and both) in which each feature indicates (i) a binary presence of the feature in a cluster group to provide up to 42 features.

In Table 1, features designated with the symbol "*" have been experimentally determined to have significant utility in the assessment of the presence or non-presence of at least one cardiac disease, medical condition, or an indication of either such as the determination of presence or non-presence of elevated LVEDP. In Table 1, features designated with the symbol "*" have been experimentally determined to have significant utility in the assessment of the presence or non-presence of at least one cardiac disease, medical condition, or an indication of either such as the determination of presence or non-presence of coronary artery disease. The list of the specific features determined to have significant utility in the assessment of the presence or non-presence of abnormal or elevated LVEDP and the presence or non-presence of significant CAD is provided in Table 7 and Table 8, respectively.

TABLE 1

| Feature in AD Waveform of Leads/Channels | Feature Type |
|---|---|
| Amplitude of the first peak (e.g., initial peak)*· ** | Amplitude |
| Amplitude of the second peak (e.g., terminal peak)** | |
| Duration of the first segment | Duration |
| Duration of the second segment | |
| Waveform area of the first segment** | Area |
| Waveform area of the second segment*** | |
| Total AD waveform area** | |
| AD waveform area ratios*· ** | |
| Morphology shape in leads X, Y, Z; dower transformed I, II, V1; PLSV transformed I, II, V1 | Waveform shape and atrial enlargement |
| LAE_II, LAE_V1, BAE_II, BAE_V1 in PLSV transformed leads II, or V1 (binary output)** | |
| LAE_II, LAE_V1, BAE_II, BAE_V1 in Dower transformed lead II, or V1 (binary output) | |
| Morphology index in leads X, Y, Z; dower transformed I, II, V1; PLSV transformed I, II, V1 (continuous output)*· ** | |
| LAE, BAE, or RAE in PLSV transformed leads II, or V1 (binary output) | Clustering |
| LAE, BAE, or RAE in Dower transformed leads II, or V1 (binary output) | |

Figures 7A, 7B, 7C:
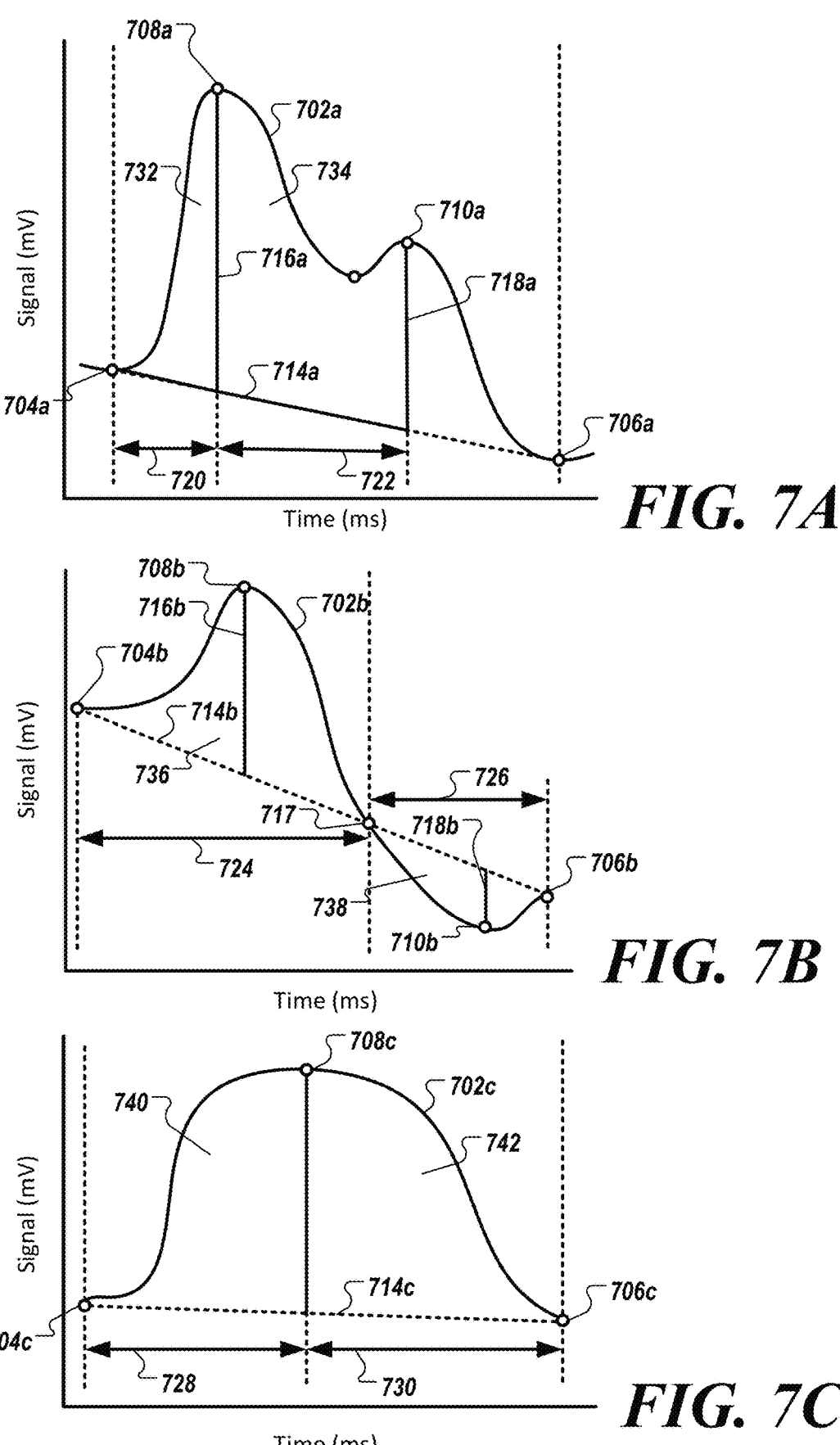
FIGS. 7A, 7B, and 7C each shows an example method of operation of the morphologic atrial depolarization waveform feature computation module of FIG. 6 in accordance with an illustrative embodiment.

FIGS. 7A, 7B, 7C show examples of atrial depolarization waveforms (shown as bifid AD waveform 702a, biphasic AD waveform 702b, and monophasic AD waveform 702c) and example waveform morphologic features (e.g., amplitude-based, duration-based, and area-based features) that can be extracted by Module 600 from such waveforms in a given lead configuration. The features are based on fiducial points such as AD onset, AD terminal or end, and local peaks that are determined in the waveforms. Module 600 can apply the same fiducial point detector for each of the waveform types and output null values for features that are not present for that waveform.

FIGS. 7A, 7B, and 7C each shows the onset fiducial point 704 (shown as 704a, 704b, 704c, respectively) and terminal fiducial point 706 (shown as 706a, 706b, 706c, respectively). Local peaks can be determined via a peak detector. In FIG. 7A, the local peaks 708a, 710a, 712a can be determined for a bifid atrial depolarization waveform 702a. In FIG. 7B, the local peaks 708a and 710b can be determined for a biphasic atrial depolarization waveform 702b. In FIG. 7C, a single peak 708c is determined for a monophasic atrial depolarization waveform 702c. An intersection line 714 (shown as 714a, 714b, 714c) can be determined between the onset fiducial points (704a, 704b, 704c, respectively) and terminal fiducial point (shown as 706a, 706b, 706c, respectively). The intersection line 714 can bound the areas of the various waveform regions—a monophasic waveform has a single region while a bifid waveform and a biphasic waveform have two regions—to which duration-based and area-based features can be computed. The intersection line 714 defines an intersection point 717 for a biphasic waveform.

Amplitude-based features. Table 1 shows two types of amplitude-based features (namely, first peak and second peak amplitudes). For the biphasic and bifid waveforms in FIGS. 7A and 7B, amplitude-based features can be determined for a first local peak 708a, 708b (also referred to as "initial peak") and a second local peak 710a, 710b (also referred to as a "terminal peak"). The first local peak 708a, 708b can be determined as the distance (shown as 716a, 716b) between the first local peak (e.g., 708a, 708b) and the intersection line (e.g., 714a, 714b). The amplitude of the second local peak 710a, 710b can be determined as the distance (shown as 718a and 718b) between the second local peak (e.g., 710a and 710b) and the intersection line (e.g., 714a and 714b). For the monophasic waveform in FIG. 7C, the amplitude of the first local peak 708c can be determined as the distance between the first peak 708c and the intersection line 714c.

Duration-based features. Table 1 shows four types of duration-based features (namely, first segment and second segment durations, total AD waveform duration, and AD waveform ratio). In the example of a bifid waveform in FIG. 7A, the first duration 720 can be determined between the onset point 704a and the first peak 708a; the second duration 722 can be determined between the first peak 708a and the second peak 710a. In the example of a biphasic waveform in FIG. 7B, the first duration 724 can be determined between the onset point 704b and the intersection point 717; the second duration 726 can be defined between the intersection point 717 and the terminal 706b. In the example of a monophasic waveform in FIG. 7C, the first duration 728 can be determined between the AD onset point 704c and the peak 708c; the second duration 730 can be determined between the peak 708c and the terminal point 706c. The duration values may be expressed in time or index.

Area-based features. Table 1 shows four area-based features (namely, waveform area of the first segment, waveform area of the second segment, total AD waveform area, and AD waveform area ratios).

For the bifid waveform in FIG. 7A, the first area feature 732 can be determined between the waveform 702a and the intersection line 714a between the onset point 704a and the first peak 708a; the second area feature 742 can be determined between the peak 708a and the second peak 710a; the total area feature can be determined between the onset 704a and terminal 706a. An area ratio feature can be determined as the ratio of the second area (734) over the sum of the first and second area (732, 734).

For the biphasic waveform in FIG. 7B, the first area feature 736 can be determined between the waveform 702b and the intersection line 714b between the onset point 704b and the intersection point 717; the second area feature 738 can be determined between the intersection point 717 and the terminal point 706b; total area feature can be determined between the onset 704b and terminal 706b. An area ratio feature can be determined as the ratio of the second area (738) over the sum of the first and second area (736, 738).

For the monophasic waveform in FIG. 7C, the first area feature 740 can be determined between the waveform 702c and the intersection line 714c between the onset point 704c and the peak 708c; the second area feature 742 can be determined between the peak 708c and the terminal point 706c; the total area feature can be determined between the onset 704c and terminal 706c (or as a sum of the first and second area features 740, 742). An area ratio feature can be determined as the ratio of the second area (742) over the sum of the first and second area (740, 742).

Figure 8:
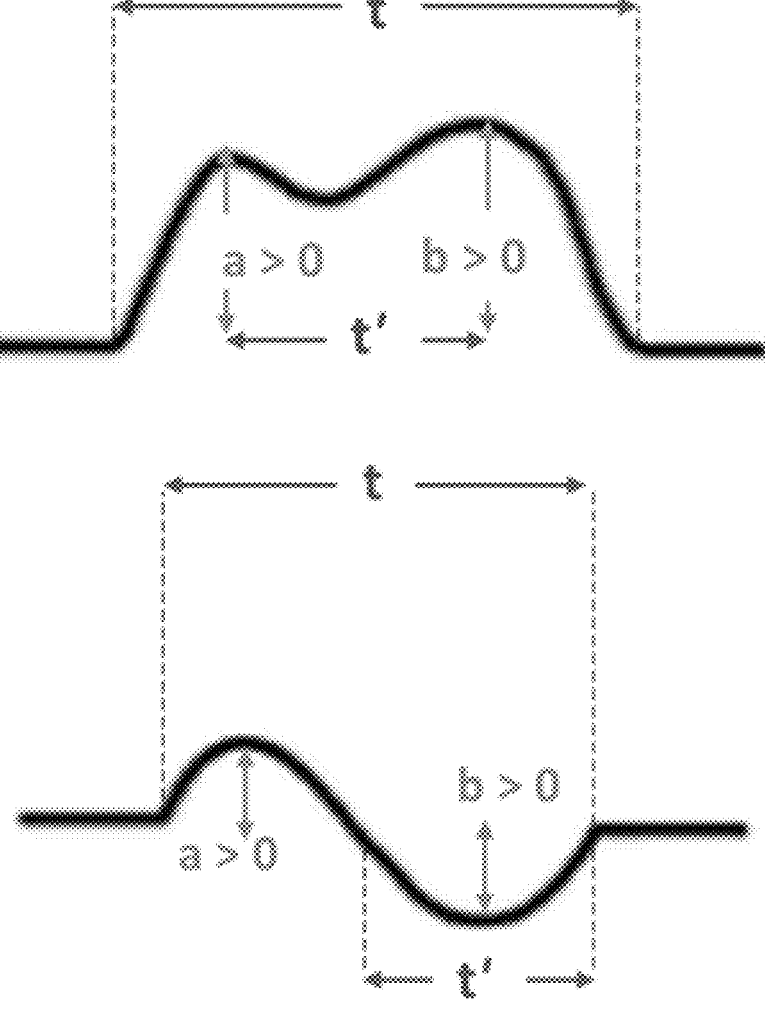
FIG. 8 shows example types of morphology-based fea-tures in accordance with an illustrative embodiment.

Morphology-based features. FIG. 8 and Table 2 show 4 example types of morphology-based features (namely, morphology/waveform shape, morphology index, and atrial enlargement (binary and continuous) features).

The first type of feature, morphology/waveform shape, provides a morphology/waveform code. Table 2 shows an example classification code for the different shapes/morphologies. Each AD waveform can be assigned a value for a given lead configuration/channel. The shape can be determined based on logic determined from the amplitude and duration features.

TABLE 2

| Code | Shape/morphology |
|---|---|
| 1 | Monophasic |
| 2 | Biphasic |
| 3 | Bifid |
| 4 | Lower Bifid |

The second type of feature, morphology index, provides a morphology index of continuous values defined by Equation 1.

$$MI = -\left(\frac{1}{2} - \frac{1}{1+e^{-\alpha}}\right) \text{ Morph Index} \qquad \text{(Equation 1)}$$

$$\text{where } \alpha = \begin{cases} 0 \ numPeak = 1 \\ sign(ab)(|b|/|a|) \ numPeak = 2 \end{cases}$$

In Equation 1, the duration-based features t and t' and amplitude-based feature a and b are shown in FIG. 8.

A third type of morphology-based features, as atrial enlargement features, provides a binary and continuous output/value of the presence of LAE_II, LAE_V1, BAE_II, and BAE_V1 in the AD waveforms. Continuous atrial enlargement features LAE_II, LAE_V1, BAE_II, and BAE_V1 can be computed per Table 3. Binary arial enlargement features provide a single binary indication of the presence of LAE_II, LAE_V1, BAE_II, and BAE_V1 for a given lead configuration data set.

TABLE 3

| Feature | Feature Description |
|---|---|
| LAE_II | $f_{LAE\_II} = MI\left(\frac{tt'}{t+t}\right)$ |
| LAE_VI | $f_{LAE\_V1} = MI\left(\frac{|b|t'}{|b|+t'}\right) = MI \times \beta$ where b is the terminal wave amplitude in µV. If no secondary wave: f = 0 |
| BAE_II | $f_{BAE\_II} = MI\left(\frac{|a|t}{|a|+t}\right)$ where a is the initial wave amplitude in µV. |

16

TABLE 3-continued

| Feature | Feature Description |
|---|---|
| BAE_VI | $f_{BAE\_V1} = MI\left(\frac{|a|t'}{|a|+t'}\right)\left(\frac{|b|t'}{|b|+t'}\right)$ where a and b are the initial and secondary waves amplitude in µV. |

In Table 3, the morphological index MI is determined per Equation 1, and the parameters a, b, t and t' correspond to that of the description of Equation 1. Atrial enlargement features may be determined for dower and PLSV lead configuration data set; the orthogonal X, Y, Z lead configuration does not have a binary definition for atrial enlargement features.

Clustering-based features. Table 1 shows clustering-based features for atrial enlargement (LAE_II, LAE_V1, BAE_II, BAE_V1) and morphology features that are stratified by gender (e.g., male, female, or both). Cluster features can be used to represent where features of a patient compares with respect to other patients across all the features. Rather than signal-based feature assessment, K-mean clustering (e.g., using k-medoids) may be used to partition a data set into k groups or clusters. In k-medoids clustering, each cluster is represented by one of the data points in the cluster or by the center of the cluster, namely the cluster medoids.

Features correlated above 0.95 can be removed. The absolute value of morphology and atrial enlargement features can be used. Features can be reduced to the first 10 PCA components. K-medoids can be generated for any number of clusters (e.g., 7). The clustering can be performed for males, females, and both gender patient groups.

Binary features can be assigned a value of "1" when a signal is located, based on the closest cluster centroid, in a given cluster number (e.g., cluster [1 . . . 7]) or "0" when the signal is not located in the cluster number.

The relative distance feature can be assigned for a signal to each cluster centroid (e.g., cluster [1 . . . 7]). The relative distance can have a range from "0" to "1" in which the value of "0" indicates closest to a centroid, and a value of "1" is furthest from the centroid.

Example Method of Computation

FIG. 9 shows a detailed implementation (900) of the morphologic atrial depolarization feature computation module 600 in accordance with an illustrative embodiment, which can be used wholly, or partially to generate morphologic atrial depolarization waveform features or parameters and their outputs to be used in machine-learned classifier to determine a metric associated with a physiological system of a patient under study. To determine the example features of Table 1, Method 900, in some embodiments, includes (i) generating (902) lead configurations of interests (e.g., generate the Dower and/or PLSV lead configuration from an acquired three-orthogonal lead configuration) (ii) isolating (906) the atrial depolarization waveforms from the respective lead configuration signal, (iii) delineating (908) landmarks in the isolated or delineated atrial depolarization waveforms, and (iv) extracting (910) features using the detected landmarks.

Dower/PLSV Transform (902). Method 900 (e.g., via Module 600) can generate Dower-transformed leads I, II, V1, and PLSV-transformed leads I, II, and VI from an acquired three-channel orthogonal lead configuration data set or a Frank lead configuration data set. Other leads of the 12-lead configuration may be generated. Tables 4 and 5 each shows conversion factors to convert signal values for a three-orthogonal channel data set to a Dower lead configuration equivalent and a PLSV lead configuration equivalent, respectively. In Table 4, the conversion factors are shown to convert the three orthogonal channel data set (shown as "Channel X," "Channel Y," and "Channel Z") via a Dower-transformed to an 12-lead configuration comprising channels "I, "II," "III," "AVR," "AVL," "AVF," "V1," "V2," "V3," "V4," "V5," and "V6." In Table 5, the conversion factors are shown to convert the three orthogonal channel data set via PLSV transformed to 8 leads of a 12-lead configuration comprising channels "V1", "V2", "V3", "V4", "V5", "V6", "I," and "II."

TABLE 4

| Dower Lead | Channel X | Channel Y | Channel Z |
| --- | --- | --- | --- |
| I | 0.632 | −0.235 | 0.059 |
| II | 0.235 | 1.066 | −0.132 |
| III | −0.397 | 1.301 | −0.191 |
| AVR | −0.434 | −0.415 | 0.037 |
| AVL | 0.515 | −0.768 | 0.125 |
| AVF | −0.081 | 1.184 | −0.162 |
| V1 | −0.515 | 0.157 | −0.917 |
| V2 | 0.044 | 0.164 | −0.139 |
| V3 | 0.882 | 0.098 | −1.277 |
| V4 | 1.213 | 0.127 | −0.601 |
| V5 | 1.125 | 0.127 | −0.086 |
| V6 | 0.831 | 0.076 | 0.230 |

TABLE 5

| PLSV Lead | Channel X | Channel Y | Channel Z |
| --- | --- | --- | --- |
| V1 | 0.147 | 0.023 | 0.184 |
| V2 | 0.058 | 0.085 | 0.163 |
| V3 | 0.037 | 0.003 | 0.190 |
| V4 | 0.139 | 0.033 | 0.119 |
| V5 | 0.232 | 0.060 | 0.023 |
| V6 | 0.226 | 0.104 | 0.043 |
| I | 0.199 | 0.146 | 0.085 |
| II | 0.018 | 0.503 | 0.130 |

In some embodiments, pre-processing operations such as sub-signaling, down-sampling, and baseline removal may be performed. Sub-signaling refers to the removal of the first, or other, portions of the signal from the analysis to eliminate transitional periods.

Atrial Depolarization Waveform Isolation (904). To isolate or delineate the atrial depolarization waveform in the cardiac signal data set, Method 900 (e.g., via Module 600) can perform a wavelet-based delineator operation. FIG. 10 shows an example wavelet-based delineator operator 904a that can be used to identify/isolate the atrial depolarization waveform from an acquired cardiac or biopotential signal. Once the time period associated with the atrial depolarization waveform is established, e.g., for the three-channel orthogonal lead data set, the same period can be referenced in the analysis of the PLSV-transformed and Dower-transformed leads I, II, V1.

In FIG. 10, method 904a includes a waveform preparation operation (1002), a peak detection operation (1004), an onset and offset detection operation (1006), and a waveform identification operation (1008). To perform the waveform preparation operation (1002), Module 600 can first convert the multiple channel signals (e.g., three channels represented as $y_x$, $y_y$, $y_z$) to a single time-series $\hat{y}$ by $\hat{y}=\sqrt{y_x^2+y_y^2+y_z^2}$. Module 904a can then identify (1004) peaks in the single time-series $\hat{y}$ signal by performing a peak detection for the ventricular depolarization (VD) peaks (also referred to as QRS peaks) in each of the cycles of $\hat{y}$. In one example, local maxima may be used, such as the findpeak function in Matlab. Module 904a can then detect (1006) an initial set of onset and offset regions for each detected VD peak using a wavelet transform operator (e.g., a continuous 1-D Morlet wavelet, Gaussian, Mexican Hat, Spline, and Mayer wavelet as a mother wavelet). Module 600 can apply the wavelet transform operator and a bandpass filter and assign the time indices when the cumulative power falls below a dynamic threshold (e.g., top 25 percentile of the cumulative power) as the VD onset and VD offset. Falsely detected fiducial points may be corrected, e.g., using an offset-onset corrector that performs a derivative of each of the signals corresponding to each of the channels of the cardiac signal data set. Method 904a can then segment (1008) the waveforms associated with atrial depolarization between the VD onset and the next consecutive cycle VD onset. From the isolated segments, ⅔ of the segment may be assigned to the waveform region associated with ventricular repolarization (T-wave), or ignored, and the remaining ⅓ can be assigned to atrial depolarization (P-wave). Other segmentation/landmark delineation may be used, for example, that described in D. B. Dubin, Rapid Interpretation of EKG's: An interactive course, 6th ed. tampa: Cover Pub, 2000.

Atrial Depolarization Landmark Determination (906). Referring to FIG. 9, to determine (906) fiducial points in the isolated or delineated atrial depolarization waveforms, Module 600 includes logic to identify initial fiducial points (e.g., onset, offset, and peaks points) in the isolated AD waveform and then adjusting the fiducial points to account for asymmetry in the waveform based on area and amplitude calculations. The operation can be performed independently for each of the 3-orthogonal channels, the Dower-transformed leads I, II, V1, and the PLSV-transformed leads I, II, V1.

Figure 11A:
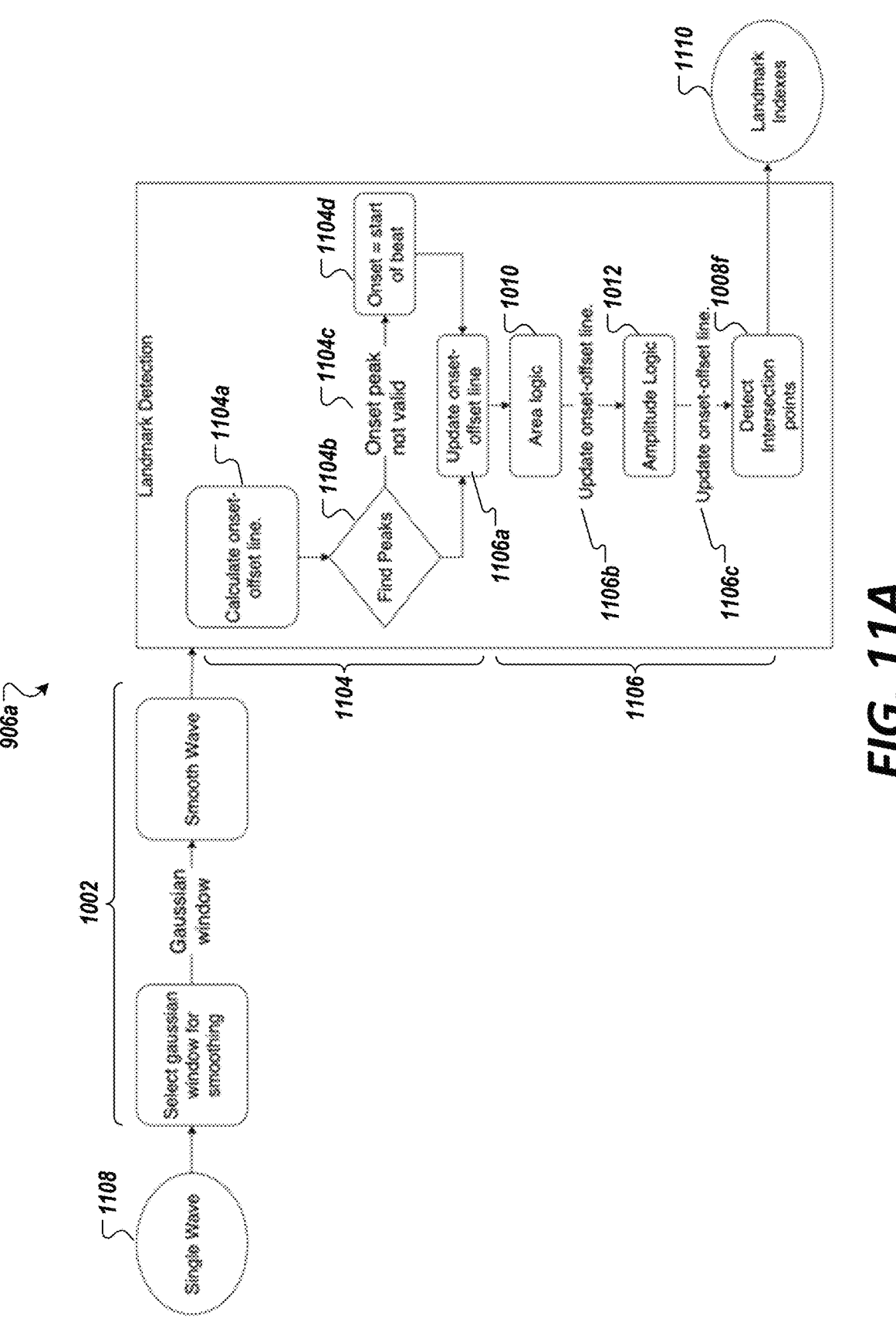
FIG. 11A shows an example method to determine fiducial points in the isolated AD waveforms in accordance with an illustrative embodiment.
Figure 11B:
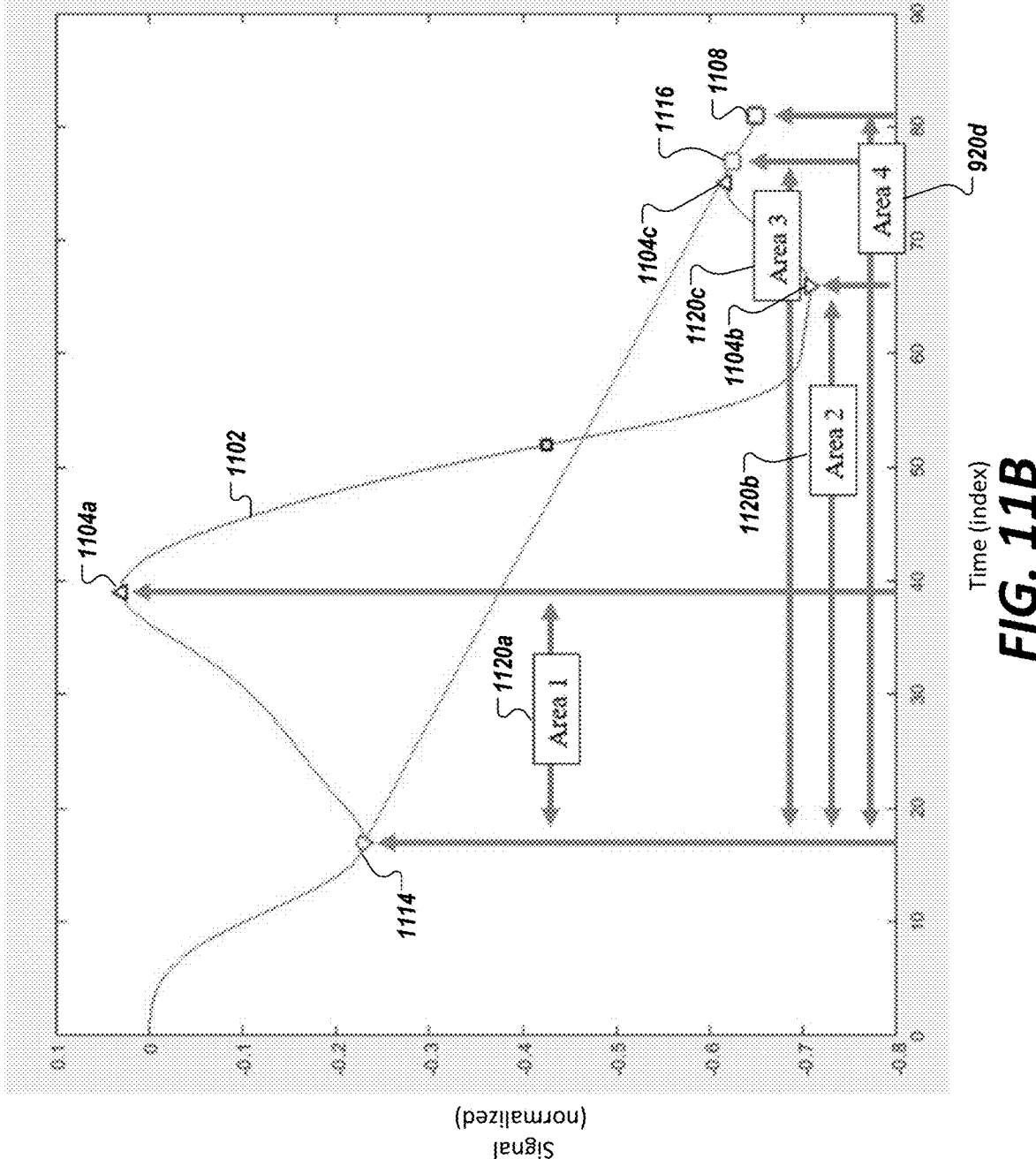
FIG. 11B shows an example biphasic waveform and landmarks identified therein using the method of FIG. 11A in accordance with an illustrative embodiment.

FIG. 11A shows an example method 906 (shown as 906a) to determine fiducial points in the isolated AD waveforms. The fiducial point detector (operating method 906a) is configured to output landmark indexes 1010 in an input waveform 1008 by (i) first smoothing (1102) the isolated AD waveform, (ii) establishing (1104) initial onset and offset fiducial points in the isolated AD waveforms (shown as 1104a, 1104b), and (iii) adjusting (1106) the fiducial points (shown as 1106a-1106f) (onset, offset, and peaks) using area and amplitude calculations. FIG. 11B shows an example biphasic waveform and landmarks identified therein using the method of FIG. 11A.

Method 906 (shown as 906a) first perform a set of smoothing operation (1102). The smooth operation reduces or prevents noise from being incorrectly identified as a noteworthy peak in the subsequent landmark detection operation. An example smoothing operation (1102) is a dynamic Gaussian filter. Depending on the morphology (bifid, biphasic, monophasic), noiseless atrial depolarization is expected to have between three and five peaks/valleys. Using an initial range of 10-50 peaks/valley, each waveform value can be tested as a Gaussian smoothing factor to determine a smoothing factor that reduces the number of resulting peaks to that expected range.

Each operation (1104b-1104d, 1010, 1012) uses a different approach to measure onset/offset accuracy. If a more accurate moment is found, then the onset-offset line is updated. The next operation gets these updated points as input. If no improvement is found by an operation then the latest update gets passed to the next operation. The line always gets updated at 1106a but 1106b and 1106c don't always trigger an update.

In the example shown in FIG. 11A, an onset offset line is first established 1104*a*. A landmark detection operator (1004) can then be performed to establish (1104*b*) the initial onset fiducial point 1114 (see FIG. 11B) and offset fiducial point 1116 (see FIG. 11B) in an atrial depolarization waveform. The beginning of atrial depolarization (namely, the onset fiducial point) has a prominent deflection that can be readily detected. If no deflection peak was found (1104*c*) at the beginning of the signal, then the logic of the landmark detection operator can set (1104*d*) the onset fiducial point with a default at the start of the windowed waveform. In addition, onset values determined outside certain physical boundaries (e.g., detected less than 35 milliseconds from the terminal fiducial point) can be considered to be unreliable and thus omitted, and the onset point can be set (1104*d*) to the default start of the windowed waveform. Following the initial onset and initial offset fiducial point determination, an updated onset offset line (also referred to herein as the intersection line) can be determined (1106*a*).

The end of atrial depolarization (namely, the offset fiducial point) can be surrounded by a greater degree of noise and thus can be difficult to detect accurately. To find a reliable position for the offset fiducial point, the landmark detection operator (1004) may include an area-based detection logic (1010) and an amplitude-based detection logic (1012). The area-based detection logic 1010 may be first performed, followed by the amplitude-based detection logic (1012). The area-based detection logic can determine areas between a current onset point and each detected peak. In FIG. 11B, the areas 1120 (shown as "area 1" 1120*a*, "area 2" 1120*b*, "area 3" 1120*c*, and "area 4" 1120*d*) can be determined between the peaks 1104*a*, 1104*b*, and 1104*c* and the initial onset point 1114. Various area logic operators may be used that considers the area below the waveform, such as the operator "trapz( )" as manufactured by MathWorks. Landmark detection operator (1004) can then classify sections with low area differences, as compared to prior calculations, as noise and drop the peak or move the offset point accordingly. In the example of FIG. 11B, "area 4" 1120*d* is dropped as a potential location for an offset due to a low calculated difference in the area.

Figure 11C:
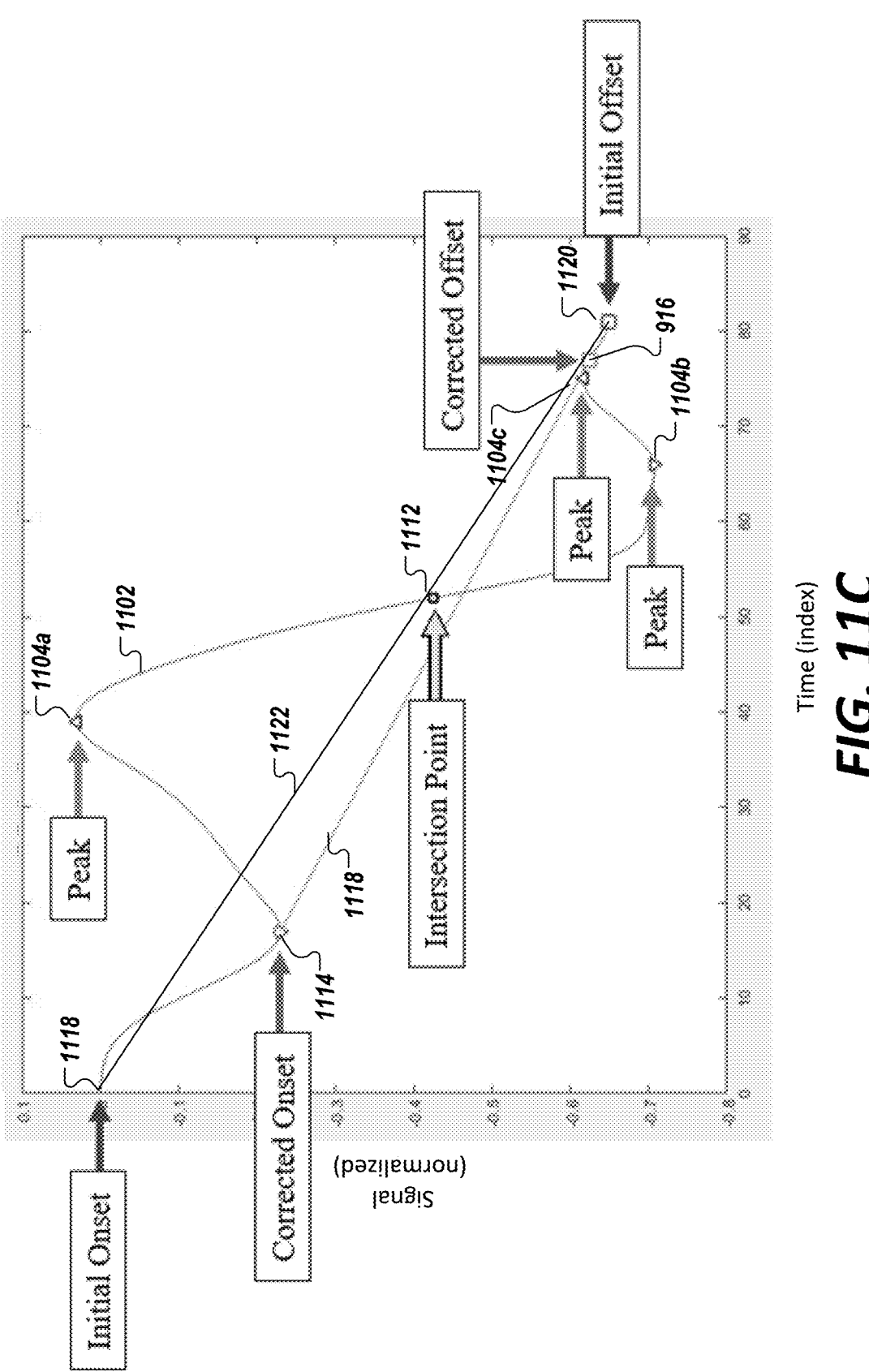
FIG. 11C shows the initial onset fiducial point and initial offset fiducial point being established along with an onset-offset line in accordance with an illustrative embodiment.

FIG. 11C shows the initial onset fiducial point (1118) and initial offset fiducial point (1120) being established (via operation 1104*a*) along with an onset-offset line 1122. Once the initial onset and offset fiducial points are set, Method 906 can adjust (1106) the fiducial points (1108) (shown as 1108*a*-1108*f*) (onset and offset) using area and then amplitude calculations. The landmark detection operator (1004) can divide/segment each AD waveform into 20 ms segments, including a forward "wave start-end" segment and a backward "wave end-start" segment. Segments having "segmentAmplitude" to "waveAmplitude" ratio less than 4 from both the forward and backward amplitude bins can be considered as the offset fiducial points. The minimum x-axis value from the forward bin and the maximum x-axis value from the backward bin can be selected, and then the greater of these two values (rounded down) can be selected as the new offset. Landmark detection operator 1004 can select (i) a minimum x-axis value from the forward bin and (ii) the maximum x-axis value from the backward bin and then select the greater of these two values (rounded down) as the new corrected offset 1116. In the example shown in FIG. 11B, the initial offset fiducial point was set at point 1108.

Lastly, the landmark detection operator 1004 is configured to detect (830) updated intersection points using an updated onset/offset line (1018) generated between the corrected onset point (1014) and the corrected offset point (1016). Where there is no fiduciary landmark in the x-axis index at the exact time index that a waveform intersects with the updated onset/offset line, the landmark detection operator 1004 is configured to select the x-axis index that is the minimum distance from the true intersection point. In the example shown in FIG. 9B, because there is no fiduciary landmark at the true intersection point, the nearest fiduciary point is selected as the intersection point (1112). Thus the intersection point (1112) was not moved from the prior determined location.

Once the fiducial points and intersection lines have been established, the amplitude, area, duration, and morphology-based features described in relation to FIG. 1 may be computed.

Experimental Results and Examples

Several development studies have been conducted to develop feature sets, and in turn, algorithms that can be used to estimate the presence or non-presence, severity, or localization of diseases, medical condition, or an indication of either. In one study, algorithms were developed for the non-invasive assessment of abnormal or elevated LVEDP. As noted above, abnormal or elevated LVEDP is an indicator of heart failure in its various forms. In another development study, algorithms and features were developed for the non-invasive assessment of coronary artery disease.

As part of these two development studies, clinical data were collected from adult human patients using a biophysical signal capture system and according to protocols described in relation to FIG. 2. The subjects underwent cardiac catheterization (the current "gold standard" tests for CAD and abnormal LVEDP evaluation) following the signal acquisition, and the catheterization results were evaluated for CAD labels and elevated LVEDP values. The collected data were stratified into separate cohorts: one for feature/algorithm development and the other for their validation.

Within the feature development phases, features were developed, including the morphologic atrial depolarization features or parameters, to extract characteristics in an analytical framework from biopotential signals (as an example of the cardiac signals discussed herein) and photo-absorption signals (as examples of the hemodynamic or photoplethysmographic discussed herein) that are intended to represent properties of the cardiovascular system. Corresponding classifiers were also developed using classifier models, linear models (e.g., Elastic Net), decision tree models (XGB Classifier, random forest models, etc.), support vector machine models, and neural network models to non-invasively estimate the presence of an elevated or abnormal LVEDP. Univariate feature selection assessments and cross-validation operations were performed to identify features for use in machine learning models (e.g., classifiers) for the specific disease indication of interest. Further description of the machine learning training and assessment are described in U.S. Provisional Patent Application No. 63/235,960, filed Aug. 23, 2021, entitled "Method and System to Non-Invasively Assess Elevated Left Ventricular End-Diastolic Pressure," which is hereby incorporated by reference herein in its entirety.

The univariate feature selection assessments evaluated many scenarios, each defined by a negative and a positive dataset pair using t-test, mutual information, and AUC-ROC evaluation. The t-test is a statistical test that can determine if there is a difference between two sample means from two populations with unknown variances. Here, the t-tests were conducted against a null hypothesis that there is no difference between the means of the feature in these groups, e.g., normal LVEDP vs. elevated (for LVEDP algorithm development); CAD– vs. CAD+ (for CAD algorithm development). A small p-value (e.g., ≤0.05) indicates strong evidence against the null hypothesis.

Mutual information (MI) operations were conducted to assess the dependence of elevated or abnormal LVEDP or significant coronary artery disease on certain features. An MI score greater than one indicates a higher dependency between the variables being evaluated. MI scores less than one indicate a lower dependency of such variables, and an MI score of zero indicates no such dependency.

A receiver operating characteristic curve, or ROC curve, illustrates the diagnostic ability of a binary classifier system as its discrimination threshold is varied. The ROC curve may be created by plotting the true positive rate (TPR) against the false positive rate (FPR) at various threshold settings. AUC-ROC quantifies the area under a receiver operating characteristic (ROC) curve—the larger this area, the more diagnostically useful the model is. The ROC, and AUC-ROC, value is considered statistically significant when the bottom end of the 95% confidence interval is greater than 0.50.

Table 6 shows an example list of the negative and a positive dataset pair used in the univariate feature selection assessments. Specifically, Table 6 shows positive datasets being defined as having an LVEDP measurement greater than 20 mmHg or 25 mmHg, and negative datasets were defined as having an LVEDP measurement less than 12 mmHg or belonging to a subject group determined to have normal LVEDP readings.

TABLE 6

| Negative Dataset | Positive Dataset |
| --- | --- |
| ≤12 (mmHg) | ≥20 (mmHg) |
| ≤12 (mmHg) | ≥25 (mmHg) |
| Normal LVEDP | ≥20 (mmHg) |
| Normal LVEDP | ≥25 (mmHg) |

Table 7 shows a list of morphologic atrial depolarization features having been determined to have utility in estimating the presence and non-presence of elevated LVEDP in an algorithm executing in a clinical evaluation system. The features of Table 7 and corresponding classifiers have been validated to have clinical performance comparable to the gold standard invasive method to measure elevated LVEDP.

TABLE 7

| Feature_name | t-test | AUC | MI |
| --- | --- | --- | --- |
| dower_waveDuration_II | 0.0026 | 0.5636 | 1.1548 |
| areaRatio_X | 0.0284 | 0.5886 | 1.5740 |
| dower_area_secondWave_V1* | 0.0103 | 0.5819 | 1.4089 |
| dower_dist_terminalSegment_I | n/s | n/s | 1.2019 |
| morphology_X | n/s | 0.5441 | 3.2187 |

FA Scenario = LVEDP <= 25 (N = 95) vs CADHealth G2 (N = 37)
*= LVEDP <= 20 (N = 95) vs CADHealth G1 (N = 122)

Table 8 shows a list of power spectral-based features having been determined to have utility in estimating the presence and non-presence of significant CAD in an algorithm executing in a clinical evaluation system. The features of Table 8 and corresponding classifiers have been validated to have clinical performance comparable to the gold standard invasive method to measure CAD.

TABLE 8

| Feature_name | t-test | AUC | MI |
| --- | --- | --- | --- |
| ampIntialPeak_X | n/s | n/s | 1.2688 |
| ampIntialPeak_Z | n/s | n/s | 1.3339 |
| ampTerminalPeak_Z | 0.0145 | 0.5202 | 1.0331 |
| area_firstWave_Z | 0.0094 | 0.5402 | 1.2690 |
| area_secondWave_Z | n/s | 0.5128 | 1.1828 |
| areaRatio_Z | n/s | 0.5215 | n/s |
| BAE_II_Z | 0.0067 | 0.5132 | 1.2666 |
| BAE_V1_Z | n/s | 0.5159 | 1.1682 |
| LAE_II_Z | 0.0034 | 0.5254 | n/s |
| LAE_V1_Z | 0.0403 | 0.5222 | n/s |
| totalArea_Z | 0.0320 | 0.5181 | n/s |
| MI_Z | 0.0013 | 0.5311 | 1.2020 |
| PLSV_ampTerminalPeak_V1 | n/s | n/s | 1.1353 |
| PLSV_area_firstWave_V1 | 0.0098 | 0.5299 | n/s |
| PLSV_area_secondWave_II | n/s | n/s | 1.1348 |
| PLSV_areaRatio_V1 | n/s | n/s | 1.1104 |
| PLSV_BAE_V1_inV1 | n/s | n/s | 1.0921 |
| PLSV_dist_initialSegment_V1 | 0.0067 | n/s | n/s |
| PLSV_morphology_I | n/s | n/s | 1.3266 |
| PLSV_totalArea_V1 | 0.0129 | 0.5454 | n/s |
| dower_ampIntialPeak_V1 | 0.0112 | n/s | n/s |
| dower_ampTerminalPeak_I | 0.0306 | n/s | n/s |
| dower_area_firstWave_V1 | 0.0326 | 0.5014 | n/s |
| dower_area_secondWave_V1 | n/s | n/s | 1.0831 |
| dower_BAE_II_inII | 0.0218 | 0.5277 | n/s |
| dower_BAE_II_inV1 | n/s | n/s | 1.0143 |
| dower_BAE_V1_inII | n/s | 0.5306 | n/s |
| dower_dist_terminalSegment_II | n/s | n/s | 1.0081 |
| dower_LAE_II | 0.0333 | n/s | 1.6387 |
| dower_LAE_II_inII | 0.0189 | 0.5277 | n/s |
| dower_LAE_V1_inII | n/s | 0.5267 | n/s |
| dower_MI_II | 0.0037 | 0.5297 | 1.2306 |
| dower_morphology_II | 0.0029 | n/s | 1.6914 |
| dower_totalArea_V1 | n/s | 0.5088 | 1.2726 |

FA scenario = significant CAD (e.g., defined as >70% blockage and/or FFR <0.8) (N = 464; 232 CAD positives and 232 CAD negatives (½ single and ½ multi-vessel disease) (½ are males and ½ are females)

The determination that certain morphologic atrial depolarization features have clinical utility in estimating the presence and non-presence of elevated LVEDP or the presence and non-presence of significant CAD provides a basis for the use of these morphologic atrial depolarization features or parameters, as well as other features described herein, in estimating for the presence or non-presence and/or severity and/or localization of other disease, medical condition, or an indication of either particularly, though not limited to, heart disease or conditions described herein.

Example Clinical Evaluation System

FIG. 12A shows an example clinical evaluation system 1200 (also referred to as a clinical and diagnostic system) that implements the modules of FIG. 1 to non-invasively compute morphologic atrial depolarization features or parameters, along with other features or parameters, to generate, via a classifier (e.g., machine-learned classifier), one or more metrics associated with the physiological state of a patient or subject according to an embodiment. Indeed, the feature modules (e.g., of FIG. 1) can be generally viewed as a part of a system (e.g., the clinical evaluation system 1200) in which any number and/or types of features may be utilized for a disease state, medical condition, an indication of either, or combination thereof that is of interest, e.g., with different embodiments having different configurations of feature modules. This is additionally illustrated in FIG. 12A, where the clinical evaluation system 1200 is of a modular design in which disease-specific add-on modules 1202 (e.g., to assess for elevated LVEDP or mPAP, CAD, PH/PAH, abnormal LVEF, HFpEF, and others described herein) are capable of being integrated alone or in multiple instances with a singular platform (i.e., a base system 1204) to realize system 1200's full operation. The modularity allows the clinical evaluation system 1200 to be designed to leverage the same synchronously acquired biophysical signals and data set and base platform to assess for the presence of several different diseases as such disease-specific algorithms are developed, thereby reducing testing and certification time and cost.

In various embodiments, different versions of the clinical evaluation system 1200 may implement the assessment system 103 (FIG. 1) by having included containing different feature computation modules that can be configured for a given disease state(s), medical condition(s), or indicating condition(s) of interest. In another embodiment, the clinical evaluation system 1200 may include more than one assessment system 103 and maybe selectively utilized to generate different scores specific to a classifier 116 of that engine 103. In this way, the modules of FIGS. 1 and 12 in a more general sense may be viewed as one configuration of a modular system in which different and/or multiple engines 103, with different and/or multiple corresponding classifiers 116, may be used depending on the configuration of module desired. As such, any number of embodiments of the modules of FIG. 1, with or without the morphologic atrial depolarization specific feature(s), may exist.

In FIG. 12A, System 1200 can analyze one or more biophysical-signal data sets (e.g., 110) using machine-learned disease-specific algorithms to assess for the likelihood of elevated LVEDP, as one example, of pathology or abnormal state. System 1200 includes hardware and software components that are designed to work together in combination to facilitate the analysis and presentation of an estimation score using the algorithm to allow a physician to use that score, e.g., to assess for the presence or non-presence of a disease state, medical condition, or an indication of either.

The base system 1204 can provide a foundation of functions and instructions upon which each add-on module 1202 (which includes the disease-specific algorithm) then interface to assess for the pathology or indicating condition. The base system 1204, as shown in the example of FIG. 12A, includes a base analytical engine or analyzer 1206, a web-service data transfer API 1208 (shown as "DTAPI" 1208), a report database 1210, a web portal service module 1213, and the data repository 111 (shown as 112a).

Data repository 112a, which can be cloud-based, stores data from the signal capture system 102 (shown as 102b). Biophysical signal capture system 102b, in some embodiments, is a reusable device designed as a single unit with a seven-channel lead set and photoplethysmogram (PPG) sensor securely attached (i.e., not removable). Signal capture system 102b, together with its hardware, firmware, and software, provides a user interface to collect patient-specific metadata entered therein (e.g., name, gender, date of birth, medical record number, height, and weight, etc.) to synchronously acquire the patient's electrical and hemodynamic signals. The signal capture system 102b may securely transmit the metadata and signal data as a single data package directly to the cloud-based data repository. The data repository 112a, in some embodiments, is a secure cloud-based database configured to accept and store the patient-specific data package and allow for its retrieval by the analytical engines or analyzer 1206 or 1214.

Base analytical engine or analyzer 1206 is a secure cloud-based processing tool that may perform quality assessments of the acquired signals (performed via "SQA" module 1216), the results of which can be communicated to the user at the point of care. The base analytical engine or analyzer 1206 may also perform pre-processing (shown via pre-processing module 1218) of the acquired biophysical signals (e.g., 110—see FIG. 1). Web portal 1213 is a secure web-based portal designed to provide healthcare providers access to their patient's reports. An example output of the web portal 1213 is shown by visualization 1236. The report databases (RD) 1212 is a secure database and may securely interface and communicate with other systems, such as a hospital or physician-hosted, remotely hosted, or remote electronic health records systems (e.g., Epic, Cerner, Allscrips, CureMD, Kareo, etc.) so that output score(s) (e.g., 118) and related information may be integrated into and saved with the patient's general health record. In some embodiments, web portal 1213 is accessed by a call center to provide the output clinical information over a telephone. Database 1212 may be accessed by other systems that can generate a report to be delivered via the mail, courier service, personal delivery, etc.

Add-on module 1202 includes a second part 1214 (also referred to herein as the analytical engine (AE) or analyzer 1214 and shown as "AE add-on module" 1214) that operates with the base analytical engine (AE) or analyzer 1206. Analytical engine (AE) or analyzer 1214 can include the main function loop of a given disease-specific algorithm, e.g., the feature computation module 1220, the classifier model 1224 (shown as "Ensemble" module 1224), and the outlier assessment and rejection module 1224 (shown as "Outlier Detection" module 1224). In certain modular configurations, the analytical engines or analyzers (e.g., 1206 and 1214) may be implemented in a single analytical engine module.

The main function loop can include instructions to (i) validate the executing environment to ensure all required environment variables values are present and (ii) execute an analysis pipeline that analyzes a new signal capture data file comprising the acquired biophysical signals to calculate the patient's score using the disease-specific algorithm. To execute the analysis pipeline, AE add-on module 1214 can include and execute instructions for the various feature modules 114 and classifier module 116 as described in relation to FIG. 1 to determine an output score (e.g., 118) of the metrics associated with the physiological state of a patient. The analysis pipeline in the AE add-on module 1214 can compute the features or parameters (shown as "Feature Computation" 1220) and identifies whether the computed features are outliers (shown as "Outlier Detection" 1222) by providing an outlier detection return for a signal-level response of outlier vs non-outlier based on the feature. The outliers may be assessed with respect to the training data set used to establish the classifier (of module 116). AE add-on module 1214 may generate the patient's output score (e.g., 118) (e.g., via classifier module 1224) using the computed values of the features and classifier models. In the example of an evaluation algorithm for the estimation of elevated LVEDP, the output score (e.g., 118) is an LVEDP score. For the estimation of CAD, the output score (e.g., 118) is a CAD score.

The clinical evaluation system 1200 can manage the data within and across components using the web-service DTAPIs 1208 (also may be referred to as HCPP web services in some embodiments). DTAPIs 1208 may be used to retrieve acquired biophysical data sets from, and to store signal quality analysis results to, the data repository 112a. DTAPIs 1208 may also be invoked to retrieve and provide the stored biophysical data files to the analytical engines or analyzers (e.g., 1206, 1214), and the results of the analytical engine's analysis of the patient signals may be transferred using DTAPI 1208 to the report database 1210. DTAPIs 1208 may also be used, upon a request by a healthcare professional, to retrieve a given patient data set to the web portal module 1213, which may present a report to the healthcare practitioner for review and interpretation in a secure web-accessible interface.

Clinical evaluation system 1200 includes one or more feature libraries 1226 that store the morphologic atrial depolarization features 120 and various other features of the feature modules 122. The feature libraries 1226 may be a part of the add-on modules 1202 (as shown in FIG. 12A) or the base system 1204 (not shown) and are accessed, in some embodiments, by the AE add-on module 1214.

Further details of the modularity of modules and various configurations are provided in U.S. Provisional Patent Application No. 63/235,960, filed Aug. 19, 2021, entitled "Modular Disease Assessment System," which is hereby incorporated by reference herein in its entirety.

Example Operation of the Modular Clinical Evaluation System

FIG. 12B shows a schematic diagram of the operation and workflow of the analytical engines or analyzers (e.g., 1206 and 1214) of the clinical evaluation system 1200 of FIG. 12A in accordance with an illustrative embodiment.

Signal quality assessment/rejection (1230). Referring to FIG. 12B, the base analytical engine or analyzer 1206 assesses (1230), via SQA module 1216, the quality of the acquired biophysical-signal data set while the analysis pipeline is executing. The results of the assessment (e.g., pass/fail) are immediately returned to the signal capture system's user interface for reading by the user. Acquired signal data that meet the signal quality requirements are deemed acceptable (i.e., "pass") and further processed and subjected to analysis for the presence of metrics associated with the pathology or indicating condition (e.g., elevated LVEDP or mPAP, CAD, PH/PAH, abnormal LVEF, HFpEF) by the AE add-on module 1214. Acquired signals deemed unacceptable are rejected (e.g., "fail"), and a notification is immediately sent to the user to inform the user to immediately obtain additional signals from the patient (see FIG. 2).

The base analytical engine or analyzer 1206 performs two sets of assessments for signal quality, one for the electrical signals and one for the hemodynamic signals. The electrical signal assessment (1230) confirms that the electrical signals are of sufficient length, that there is a lack of high-frequency noise (e.g., above 170 Hz), and that there is no power line noise from the environment. The hemodynamic signal assessment (1230) confirms that the percentage of outliers in the hemodynamic data set is below a pre-defined threshold and that the percentage and maximum duration that the signals of the hemodynamic data set are railed or saturated is below a pre-defined threshold.

Feature Value Computation (1232). The AE add-on module 1214 performs feature extraction and computation to calculate feature output values. In the example of the LVEDP algorithm, the AE add-on module 1214 determines, in some embodiments, a total of 446 feature outputs belonging to 18 different feature families (e.g., generated in modules 120 and 122), including the morphologic atrial depolarization features (e.g., generated in module 120). For the CAD algorithm, an example implementation of the AE add-on module 1214 determine a set of features, including 456 features corresponding to the same 18 feature families.

Additional descriptions of the various features, including those used in the LVEDP algorithm and other features and their feature families, are described in U.S. Provisional Patent Application No. 63/235,960, filed Aug. 23, 2021, entitled "Method and System to Non-Invasively Assess Elevated Left Ventricular End-Diastolic Pressure"; U.S. Provisional Patent Application No. 63/236,072, filed Aug. 23, 2021, entitled "Methods and Systems for Engineering Visual Features From Biophysical Signals for Use in Characterizing Physiological Systems"; U.S. Provisional Patent Application No. 63/235,963, filed Aug. 23, 2021, entitled "Methods and Systems for Engineering Power Spectral Features From Biophysical Signals for Use in Characterizing Physiological Systems"; U.S. Provisional Patent Application No. 63/235,966, filed Aug. 23, 2021, entitled "Method and System for Engineering Rate-Related Features_From Biophysical Signals for Use in Characterizing Physiological Systems"; U.S. Provisional Patent Application No. 63/235,968, filed Aug. 23, 2021, entitled "Methods and Systems for Engineering Wavelet-Based Features From Biophysical Signals for Use in Characterizing Physiological Systems"; U.S. Provisional Patent Application No. 63/130, 324, titled "Method and System to Assess Disease Using Cycle Variability Analysis of Cardiac and Photoplethysmographic Signals"; U.S. Provisional Patent Application No. 63/235,971, filed Aug. 23, 2021, entitled "Methods and Systems for Engineering photoplethysmographic Waveform Features for Use in Characterizing Physiological Systems"; U.S. Provisional Patent Application No. 63/235,974, filed Aug. 23, 2021, entitled "Methods and Systems for Engineering Conduction Deviation Features From Biophysical Signals for Use in Characterizing Physiological Systems", each of which is hereby incorporated by reference herein in its entirety.

Classifier Output Computation (1234). The AE add-on module 1214 then uses the calculated feature outputs in classifier models (e.g., machine-learned classifier models) to generate a set of model scores. The AE add-on module 1214 joins the set of model scores in an ensemble of the constituent models, which, in some embodiments, averages the output of the classifier models as shown in Equation 2 in the example of the LVEDP algorithm.

$$\text{Ensemble estimation} = \frac{\text{Model}_1 + \text{Model}_2 + \ldots + \text{Model}_n}{n} \quad \text{(Equation 2)}$$

In some embodiments, classifier models may include models that are developed based on ML techniques described in U.S. Patent Publication No. 20190026430, entitled "Discovering Novel Features to Use in Machine Learning Techniques, such as Machine Learning Techniques for Diagnosing Medical Conditions"; or U.S. Patent Publication No. 20190026431, entitled "Discovering Genomes to Use in Machine Learning Techniques," each of which is hereby incorporated by reference herein in its entirety.

In the example of the LVEDP algorithm, thirteen (13) machine-learned classifier models are each calculated using the calculated feature outputs. The 13 classifier models include four ElasticNet machine-learned classifier models [9], four RandomForestClassifier machine-learned classifier models [10], and five extreme gradient boosting (XGB) classifier models [11]. In some embodiments, the patient's metadata information, such as age, gender, BMI value, may be used. The output of the ensemble estimation may be a continuous score. The score may be shifted to a threshold value of zero by subtracting the threshold value for presentation within the web portal. The threshold value may be selected as a trade-off between sensitivity and specificity. The threshold may be defined within the algorithm and used as the determination point for test positive (e.g., "Likely Elevated LVEDP") and test negative (e.g., "Not Likely Elevated LVEDP") condition.

In some embodiments, the analytical engine or analyzer can fuse the set of model scores with a body mass index-based adjustment or an adjustment based on age or gender. For example, the analytical engine or analyzer can average the model estimation with a sigmoid function of the patient BMI having the form $$\text{sigmoid}(x) = \frac{1}{1 + e^{-x}}.$$

Physician Portal Visualization (1236). The patient's report may include a visualization 1236 of the acquired patient data and signals and the results of the disease analyses. The analyses are presented, in some embodiments, in multiple views in the report. In the example shown in FIG. 12B, the visualization 1236 includes a score summary section 1240 (shown as "Patient LVEDP Score Summary" section 1240), a threshold section 1242 (shown as "LVEDP Threshold Statistics" section 1242), and a frequency distribution section 1244 (shown as "Frequency Distribution" section 1208). A healthcare provider, e.g., a physician, can review the report and interpret it to provide a diagnosis of the disease or to generate a treatment plan.

The healthcare portal may list a report for a patient if a given patient's acquired signal data set meets the signal quality standard. The report may indicate a disease-specific result (e.g., elevated LVEDP) being available if the signal analysis could be performed. The patient's estimated score (shown via visual element 118a, 118b, 118c) for the disease-specific analysis may be interpreted relative to an established threshold.

In the score summary section 1240 shown in the example of FIG. 12B, the patient's score 118a and associated threshold are superimposed on a two-tone color bar (e.g., shown in section 1240) with the threshold located at the center of the bar with a defined value of "0" representing the delineation between test positive and test negative. The left of the threshold may be lightly shaded light and indicates a negative test result (e.g., "Not Likely Elevated LVEDP") while to the right of the threshold may be darkly shaded to indicate a positive test result (e.g., "Likely Elevated LVEDP").

The threshold section 1242 shows reported statistics of the threshold as provided to a validation population that defines the sensitivity and specificity for the estimation of the patient score (e.g., 118). The threshold is the same for every test regardless of the individual patient's score (e.g., 118), meaning that every score, positive or negative, maybe interpreted for accuracy in view of the provided sensitivity and specificity information. The score may change for a given disease-specific analysis as well with the updating of the clinical evaluation.

The frequency distribution section 1244 illustrates the distribution of all patients in two validation populations (e.g., (i) a non-elevated population to indicate the likelihood of a false positive estimation and (ii) an elevated population to indicate a likelihood of a false negative estimation). The graphs (1246, 1248) are presented as smooth histograms to provide context for interpreting the patient's score 118 (e.g., 118b, 118c) relative to the test performance validation population patients.

The frequency distribution section 1240 includes a first graph 1246 (shown as "Non-Elevated LVEDP Population" 1246) that shows the score (118b), indicating the likelihood of the non-presence of the disease, condition, or indication, within a distribution of a validation population having non-presence of that disease, condition, or indication and a second graph 1248 (shown as "Elevated LVEDP Population" 1248) that shows the score (118c), indicates the likelihood of the presence of the disease, condition, or indication, within a distribution of validation population having the presence of that disease, condition, or indication. In the example of the assessment of elevated LVDEP, the first graph 1246 shows a non-elevated LVEDP distribution of the validation population that identifies the true negative (TN) and false positive (FP) areas. The second graph 1248 shows an elevated LVEDP distribution of the validation population that identifies the false negative (TN) and true positive (FP) areas.

The frequency distribution section 1240 also includes interpretative text of the patient's score relative to other patients in a validation population group (as a percentage). In this example, the patient has an LVEDP score of −0.1208, which is located to the left side of the LVEDP threshold, indicating that the patient has "Not Likely Elevated LVEDP."

The report may be presented in the healthcare portal, e.g., to be used by a physician or healthcare provider in their diagnosis for indications of left-heart failure. The indications include, in some embodiments, a probability or a severity score for the presence of a disease, medical condition, or an indication of either.

Outlier Assessment and Rejection Detection (1238). Following the AE add-on module 1214 computing the feature value outputs (in process 1232) and prior to their application to the classifier models (in process 1234), the AE add-on module 1214 is configured in some embodiments to perform outlier analysis (shown in process 1238) of the feature value outputs. Outlier analysis evaluation process 1238 executes a machine-learned outlier detection module (ODM), in some embodiments, to identify and exclude anomalous acquired biophysical signals by identifying and excluding anomalous feature output values in reference to the feature values generated from the validation and training data. The outlier detection module assesses for outliers that present themselves within sparse clusters at isolated regions that are out of distribution from the rest of the observations. Process 1238 can reduce the risk that outlier signals are inappropriately applied to the classifier models and produce inaccurate evaluations to be viewed by the patient or healthcare provider. The accuracy of the outlier module has been verified using hold-out validation sets in which the ODM is able to identify all the labeled outliers in a test set with the acceptable outlier detection rate (ODR) generalization.

While the methods and systems have been described in connection with certain embodiments and specific examples, it is not intended that the scope be limited to the particular embodiments set forth, as the embodiments herein are intended in all respects to be illustrative rather than restrictive. The morphologic atrial depolarization features discussed herein may ultimately be employed to make, or to assist a physician or other healthcare provider in making, noninvasive diagnoses or determinations of the presence or non-presence and/or severity of other diseases, medical conditions, or indication of either, such as, e.g., coronary artery disease, pulmonary hypertension and other pathologies as described herein using similar or other development approaches. In addition, the example analysis, including the morphologic atrial depolarization features, can be used in the diagnosis and treatment of other cardiac-related pathologies and indicating conditions as well as neurological-related pathologies and indicating conditions, such assessment can be applied to the diagnosis and treatment (including, surgical, minimally invasive, and/or pharmacologic treatment) of any pathologies or indicating conditions in which a biophysical signal is involved in any relevant system of a living body. One example in the cardiac context is the diagnosis of CAD, and other diseases, medical condition, or indicating conditions disclosed herein and its treatment by any number of therapies, alone or in combination, such as the placement of a stent in a coronary artery, the performance of an atherectomy, angioplasty, prescription of drug therapy, and/or the prescription of exercise, nutritional and other lifestyle changes, etc. Other cardiac-related pathologies or indicating conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other diseases such as blood or other disorders), as well as other cardiac-related pathologies, indicating conditions and/or diseases. Non-limiting examples of neurological-related diseases, pathologies or indicating conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/nerve injury, chronic traumatic encephalopathy, cluster headaches, migraine headaches, neuropathy (in its various forms, including peripheral neuropathy), phantom limb/pain, chronic fatigue syndrome, acute and/or chronic pain (including back pain, failed back surgery syndrome, etc.), dyskinesia, anxiety disorders, indicating conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/indicating conditions and vision-related diseases/indicating conditions.

In addition, the clinical evaluation system described herein may be configured to analyze biophysical signals such as an electrocardiogram (ECG), electroencephalogram (EEG), gamma synchrony, respiratory function signals, pulse oximetry signals, perfusion data signals; quasi-periodic biological signals, fetal ECG signals, blood pressure signals; cardiac magnetic field signals, heart rate signals, among others.

Further examples of processing that may be used with the exemplified method and system disclosed herein are described in: U.S. Pat. Nos. 9,289,150; 9,655,536; 9,968,275; 8,923,958; 9,408,543; 9,955,883; 9,737,229; 10,039,468; 9,597,021; 9,968,265; 9,910,964; 10,672,518; 10,566,091; 10,566,092; 10,542,897; 10,362,950; 10,292,596; 10,806,349; U.S. Patent Publication nos. 2020/0335217; 2020/0229724; 2019/0214137; 2018/0249960; 2019/0200893; 2019/0384757; 2020/0211713; 2019/0365265; 2020/0205739; 2020/0205745; 2019/0026430; 2019/0026431; PCT Publication nos. WO2017/033164; WO2017/221221; WO2019/130272; WO2018/158749; WO2019/077414; WO2019/130273; WO2019/244043; WO2020/136569; WO2019/234587; WO2020/136570; WO2020/136571; U.S. patent application Ser. Nos. 16/831,264; 16/831,380; 17/132,869; PCT Application nos. PCT/

IB2020/052889; PCT/IB2020/052890, each of which is hereby incorporated by reference herein in its entirety.

What is claimed is:

1. A method for non-invasively assessing a cardiac disease state or condition of a subject, the method comprising:
obtaining, by one or more processors, a biophysical signal data set of the subject, wherein the biophysical signal data set comprises two or more signal types that are synchronously captured via a non-invasive biophysical signal recorder or capture system and includes a multi-channel cardiac signal;
transforming, by the one or more processors, the multi-channel cardiac signal into a single time-series signal;
determining, by the one or more processors, atrial depolarization-associated waveforms from the single time-series signal;
determining, by the one or more processors and using a landmark detection operator, fiduciary landmarks in the atrial depolarization-associated waveforms, wherein the landmark detection operator dynamically adjusts onset and offset fiduciary landmarks to account for asymmetry in the atrial depolarization-associated waveforms based on area and amplitude calculations;
determining, by the one or more processors, one or more values of one or more features extracted using the fiduciary landmarks, wherein the one or more features include a feature determined using a clustering operator;
determining, by the one or more processors, values of one or more waveform-associated properties of atrial enlargement from the one or more extracted features; and
determining, by the one or more processors, an estimated value for presence or non-presence of the cardiac disease state or condition based, in part, on the determined values of the one or more waveform-associated properties, wherein the estimated value for the cardiac disease state or condition is used in a model to non-invasively estimate presence or non-presence of the cardiac disease state or condition,
wherein the estimated value is subsequently outputted for use in a diagnosis of the cardiac disease state or condition or to direct treatment of the cardiac disease state or condition.

2. The method of claim 1, wherein the values of one or more waveform-associated properties are associated with Left Atrial Enlargement (LAE), Right Atrial Enlargement (RAE), Bi-atrial Enlargement (BAE), or a combination of two or more thereof and are assessed from atrial depolarization-associated waveforms identified in at least one of the multi-channel cardiac signal.

3. The method of claim 1, wherein the one or more features are selected from the group consisting of:
a feature associated with amplitude of a peak determined in the atrial depolarization-associated waveforms;
a feature associated with duration of a determined portion of the atrial depolarization-associated waveforms;
a feature associated with an assessed area of a determined portion of the atrial depolarization-associated waveforms; and
a feature associated with morphology of the atrial depolarization-associated waveforms.

4. The method of claim 3, wherein the one or more features include the feature associated with the assessed area of the determined portion of the atrial depolarization-associated waveforms, wherein the assessed area includes at least one of:

an assessed area of an assessed first wave;

an assessed area of an assessed second wave;

a total area of the first and second wave; and a ratio derived from assessed areas of the first and second waves.

5. The method of claim 3, wherein the one or more features include the feature associated with the duration of the determined portion of the atrial depolarization-associated waveforms, wherein the duration includes i) a duration from a maximum peak in the waveform to an assessed onset or offset landmark in the waveform;

wherein the duration includes i) a duration from an assessed intersect landmark in the waveform to an assessed onset or offset landmark in the waveform; and wherein the duration includes i) a duration from a maximum peak in the waveform to an assessed onset landmark or an assessed second maximum peak in the waveform.

6. The method of claim 3, wherein the one or more features include a feature associated with the morphology of the atrial depolarization-associated waveforms, wherein said feature associated with the morphology of the atrial depolarization-associated waveforms generates a plurality of continuous index values for one or more atrial enlargement criteria, wherein each of the plurality of continuous index values encodes for an atrial enlargement criterion.

7. The method of claim 6, wherein the plurality of continuous index values encode an index value for an assessed monophasic-shaped morphology of the atrial depolarization-associated waveforms, an assessed biphasic-shaped morphology of the atrial depolarization-associated waveforms, an assessed bifid-shaped morphology of the atrial depolarization-associated waveforms, and an assessed lower bifid-shaped morphology of the atrial depolarization-associated waveforms.

8. The method of claim 6, wherein the plurality of continuous index values are encoded for a given lead configuration selected from the group consisting of Frank lead X, Frank lead Y, Frank lead Z, Dower-transformed lead I, Dower-transformed lead II, Dower-transformed lead V1, PLSV-transformed lead I, PLSV-transformed lead II, and PLSV-transformed lead V1.

9. The method of claim 1, wherein the one or more features include the feature determined using a clustering operator performed on one or more features associated with i) a feature associated with amplitude of a peak determined in the atrial depolarization-associated waveforms, ii) a feature associated with duration of a determined portion of the atrial depolarization-associated waveforms, iii) a feature associated with an assessed area of a determined portion of the atrial depolarization-associated waveforms; and iv) a feature associated with morphology of the atrial depolarization-associated waveforms, wherein the clustering operator is performed on dataset based on gender of the subject.

10. The method of claim 1 further comprising:

causing, by the one or more processors, generation of a visualization of the estimated value for the presence or non-presence of the cardiac disease state or abnormal condition, wherein the generated visualization is rendered and displayed at a display of a computing device and/or presented in a report.

11. The method of claim 1, wherein the values of the one or more waveform-associated properties of atrial enlargement are used in the model selected from the group consisting of a linear model, a decision tree model, a random forest model, a support vector machine model, a neural network model.

12. The method of claim 1, wherein the model further includes features selected from the group consisting of:

one or more depolarization or repolarization wave propagation associated features;

one or more depolarization wave propagation deviation associated features;

one or more cycle variability associated features;

one or more dynamical system associated features;

one or more cardiac waveform topologic and variations associated features;

one or more PPG waveform topologic and variations associated features;

one or more cardiac or PPG signal power spectral density associated features;

one or more cardiac or PPG signal visual associated features; and one or more predictability features.

13. The method of claim 1, wherein the cardiac disease state or abnormal condition is selected from the group consisting of coronary artery disease, pulmonary hypertension, pulmonary arterial hypertension, pulmonary hypertension due to left heart disease, rare disorders that lead to pulmonary hypertension, left ventricular heart failure or left-sided heart failure, right ventricular heart failure or right-sided heart failure, systolic heart failure, diastolic heart failure, ischemic heart disease, and arrhythmia.

14. The method of claim 1 further comprising:

acquiring, by one or more acquisition circuits of a measurement system, voltage gradient signals over one or more channels, wherein the voltage gradient signals are acquired at a frequency greater than about 1 kHz; and generating, by the one or more acquisition circuits, the obtained biophysical data set from the acquired voltage gradient signals.

15. The method of claim 14, wherein the voltage gradient signals include one or more photoplethysmographic signals.

16. The method of claim 1, wherein the one or more processors are located in a cloud platform.

17. The method of claim 1, wherein the one or more processors are located in a local computing device.

18. A system comprising:

a processor; and a memory having instructions stored thereon, wherein execution of the instructions by the processor causes the processor to:

obtain a biophysical signal data set of a subject, wherein the biophysical signal data set comprises two or more signal types that are synchronously captured via a non-invasive biophysical signal recorder or capture system and includes a multi-channel cardiac signal;

transform the multi-channel cardiac signal into a single time-series signal;

determine atrial depolarization-associated waveforms from the single time-series signal;

determine, using a landmark detection operator, fiduciary landmarks in the atrial depolarization-associated waveforms, wherein the landmark detection operator dynamically adjusts onset and offset fiduciary landmarks to account for asymmetry in the atrial depolarization-associated waveforms based on area and amplitude calculations;

determine one or more values of one or more features extracted using the fiduciary landmarks, wherein the one or more features include a feature determined using a clustering operator;

determine values of one or more waveform-associated properties of atrial enlargement from the one or more extracted features; and determine an estimated value for presence or non-presence of a cardiac disease state or condition based, in part, on the determined values of the one or more waveform-associated properties, wherein the estimated value for the cardiac disease state or condition is used in a model to non-invasively estimate presence or non-presence of the cardiac disease state or condition, wherein the estimated value is subsequently outputted for use in a diagnosis of the cardiac disease state or condition or to direct treatment of the cardiac disease state or condition.

19. A non-transitory computer-readable medium having instructions stored thereon, wherein execution of the instructions by a processor causes the processor to:

obtain a biophysical signal data set of a subject, wherein the biophysical signal data set comprises two or more signal types that are synchronously captured via a non-invasive biophysical signal recorder or capture system and includes a multi-channel cardiac signal;

transform the multi-channel cardiac signal into a single time-series signal;

determine atrial depolarization-associated waveforms from the single time-series signal;

determine, using a landmark detection operator, fiduciary landmarks in the atrial depolarization-associated waveforms, wherein the landmark detection operator dynamically adjusts onset and offset fiduciary landmarks to account for asymmetry in the atrial depolarization-associated waveforms based on area and amplitude calculations;

determine one or more values of one or more features extracted using the fiduciary landmarks, wherein the one or more features include a feature determined using a clustering operator;

determine values of one or more waveform-associated properties of atrial enlargement from the one or more extracted features; and determine an estimated value for presence or non-presence of a cardiac disease state or condition based, in part, on the determined values of the one or more waveform-associated properties, wherein the estimated value for the cardiac disease state or condition is used in a model to non-invasively estimate presence or non-presence of the cardiac disease state or condition, wherein the estimated value is subsequently outputted for use in a diagnosis of the cardiac disease state or condition or to direct treatment of the cardiac disease state or condition.

* * * * *